(12) United States Patent
Degli-Esposti et al.

(10) Patent No.: US 11,986,495 B2
(45) Date of Patent: May 21, 2024

(54) METHOD OF TREATMENT

(71) Applicants: Lions Eye Institute Limited, Nedlands (AU); QIMR Berghofer Medical Research Institute, Herston (AU)

(72) Inventors: Mariapia A. Degli-Esposti, Nedlands (AU); Geoffrey R. Hill, Hawthorne (AU); Christopher E. Andoniou, Woodbridge (AU); Peter Fleming, Samson (AU)

(73) Assignees: Lions Eye Institute Limited, Nedlands (AU); QIMR Berghofer Medical Research Institute, Herston (AU)

( * ) Notice: Subject to any disclaimer, the term of this patent is extended or adjusted under 35 U.S.C. 154(b) by 663 days.

(21) Appl. No.: 16/767,060

(22) PCT Filed: Nov. 28, 2018

(86) PCT No.: PCT/AU2018/051271
§ 371 (c)(1),
(2) Date: May 26, 2020

(87) PCT Pub. No.: WO2019/104384
PCT Pub. Date: Jun. 6, 2019

(65) Prior Publication Data
US 2020/0289559 A1 Sep. 17, 2020

(30) Foreign Application Priority Data
Nov. 28, 2017 (AU) ................................ 2017904807

(51) Int. Cl.
A61K 35/16 (2015.01)
A61P 31/20 (2006.01)
C07K 16/42 (2006.01)

(52) U.S. Cl.
CPC .............. *A61K 35/16* (2013.01); *A61P 31/20* (2018.01); *C07K 16/4283* (2013.01)

(58) Field of Classification Search
None
See application file for complete search history.

(56) References Cited

PUBLICATIONS

Aguado et al., Prospective Randomized Trial of Efficacy of Ganciclovir versus That of Anti-Cytomegalovirus (CMV) Immunoglobulin To Prevent CMV Disease in CMV-Seropositive Heart Transplant Recipients Treated with OKT3, 1995, Antimicrobial Agents and Chemotherapy, vol. 39, No. 7, pp. 1643-1645.*
Feltracco et al., Blood loss, predictors of bleeding, transfusion practice and strategies of blood cell salvaging during liver transplantation, 2013, World J Hepatol, vol. 5, No. 1, pp. 1-15.*
Carbone, The Immunology of Posttransplant CMV Infection: Potential Effect of CMV Immunoglobulins on Distinct Components of the Immune Response to CMV, 2016, Transplantation, vol. 100, pp. S11-S18.*
Binder, et al.; "Identification of human cytomegalovirus variants by analysis of single strand conformation polymorphism and DNA sequencing of the envelope glycoprotein B gene region-distribution frequency in liver transplant recipients"; Journal of Virological Methods, 78:153-162 (1999).
Bruedigam, et al.; "Telomerase Inhibition Effectively Targets Mouse and Human AML Stem Cells and Delays Relapse following Chemotherapy"; Cell Stem Cell, 15: 775-790 (2014).
Cassese, et al.; "Plasma Cell Survival Is Mediated by Synergistic Effects of Cytokines and Adhesion- Dependent Signals"; Journal of Immunology, 171: 1684-1690 (2003).
Cekinović, et al.; "Passive Immunization Reduces Murine Cytomegalovirus-Induced Brain Pathology in Newborn Mice"; Journal of Virology, 82(24): 12172-12180 (2008).
Coaquette, et al.; "Mixed Cytomegalovirus Glycoprotein B Genotypes in Immunocompromised Patients"; Clinical Infectious Diseases, 39:155-161 (2004).
Cooke, et al.; "An Experimental Model of Idiopathic Pneumonia Syndrome After Bone Marrow Transplantation: I. The Roles of Minor H Antigens and Endotoxin" Blood, 88: 3230-3239 (1996).
Cui, et al.; "Antibody inhibition of human cytomegalovirus spread in epithelial cell cultures"; Journal of Virological Methods, 192: 44-50 (2013).
Filipovich, et al.; "Circulating Cytomegalovirus (CMV) Neutralizing Activity in Bone Marrow Transplant Recipients: Comparison of Passive Immunity in a Randomized Study of Four Intravenous IgG Products Administered to CMV-Seronegative Patients"; Blood, 80(10): 26656-2660 (1992).
Franklin, et al.; "Cytomegalovirus reactivation in patients with refractory checkpoint inhibitor-induced colitis"; European Journal of Cancer, 86: 248-256 (2017).
Hill, et al.; "Successful Immunotherapy of HCMV Disease Using Virus-Specific T Cells Expanded from an Allogeneic Stem Cell Transplant Recipient"; American Journal of Transplantation, 10(1): 173-179 (2010).
Lawson, et al.; "Antibody Responses to Murine Cytomegalovirus in Genetically Resistant and Susceptible Strains of Mice"; Journal of General Virology, 69: 1987-1998 (1988).
Novak, et al.; "Cytomegalovirus Strain Diversity in Seropositive Women"; Journal of Clinical Microbiology, 46(3): 882-886 (2008).
Palladino, et al.; "Virus-Neutralizing Antibodies of Immunoglobulin G (IgG) but Not of IgM or IgA Isotypes Can Cure Influenza Virus Pneumonia in SCID Mice"; Journal of Virology, 69: 2075-2081 (1995).
Rasmussen, et al.; "Cytomegalovirus gB Genotype Distribution Differs in Human Immunodeficiency Virus-Infected Patients and Immunocompromised Allograft Recipients" Journal of Infection and Disease, 175(1):179-184 (1997).
Schmidt, et al.; "A Randomized, Controlled Trial of Prophylactic Ganciclovir for Cytomegalovirus Pulmonary Infection in Recipients of Allogeneic Bone Marrow Transplants"; The New England Journal of Medicine, 324 (1991).

(Continued)

Primary Examiner — Benjamin P Blumel
(74) Attorney, Agent, or Firm — Bozicevic, Field & Francis LLP; Mandar A. Joshi

(57) ABSTRACT

This invention relates generally to the inhibition of cytomegalovirus (CMV) reactivation in immunosuppressed subjects, including subjects receiving hematopoietic or solid organ transplants. The present invention is particularly relevant for the treatment of CMV reactivation or infection in subjects with graft-versus-hosts disease (GVHD) or under immunosuppressive therapy.

13 Claims, 24 Drawing Sheets

(56) References Cited

PUBLICATIONS

Takai; "Roles OF Fc Receptors in Autoimmunity"; Nature Reviews Immunology, 2: 580-592 (2002).

Voigt, et al.; "Murine cytomegalovirus m157 mutation and variation leads to immune evasion of natural killer cells"; Proceedings of the National Academy of Sciences USA, 100(23):13483-13488 (2003).

Wikstrom, et al.; "Acute GVHD results in a severe DC defect that prevents T-cell priming and leads to fulminant cytomegalovirus disease in mice"; Blood, 126(12): 1503-1514 (2015).

Wirtz, et al.; "Polyclonal cytomegalovirus-specific antibodies not only prevent virus dissemination from the portal of entry but also inhibit focal virus spread within target tissues"; Medical Microbiology and Immunology, 197(2): 151-158 (2008).

\* cited by examiner

E

F

G

H

I

A

B

C

D

H

I

C

D

E

F

A

B

C

D

E

F

D

E

F

G

A

B

C

D

E

F

G

K

METHOD OF TREATMENT

FIELD OF THE INVENTION

This invention relates generally to the inhibition of cytomegalovirus (CMV) reactivation in immunosuppressed subjects, including subjects receiving hematopoietic or solid organ transplants. The present invention is particularly relevant for the treatment of CMV reactivation or infection in subjects with graft-versus-hosts disease (GVHD) or under immunosuppressive therapy.

BACKGROUND OF THE INVENTION

Hematologic and solid organ transplantation provides a curative treatment option for many high-risk cancerous and non-cancerous diseases but its full therapeutic potential is currently limited by relapse of malignancy and transplant-related complications, particularly graft-versus-host disease (GVHD), graft rejection and opportunistic infections.

Viruses are a common cause of infection in the period post transplantation. Adenovirus infections can cause multi-organ disease including pneumonia, encephalitis, hepatitis, gastroenteritis and haemorrhagic cystitis. Respiratory syncytial virus and influenza can cause severe respiratory tract infections. Furthermore, there is a significant risk of secondary viral infection from a variety of viruses including BK-virus infections associated with haemorrhagic cystitis, varicella zoster virus (VZV) and viruses from the herpesvirus family Epstein-Barr virus, (EBV), Herpes simplex virus (HS), human herpesvirus-6 (HHV-6) and cytomegalovirus (CMV), amongst others. CMV infections are very common post-transplant and pose a significant burden on transplant outcome. Multiple risk factors are associated with viral reactivation and infection.

CMV is a ubiquitous herpesvirus with 40-90% seroprevalence. Primary CMV infection is generally asymptomatic in healthy individuals, but life-long latency ensues following infection. In immune compromised settings, such as allogenic bone marrow transplantation (BMT) or hematopoietic stem cell transplantation, CMV reactivation is common and results in significant morbidity and mortality. Reactivation is commonly associated with multi-organ failure and the prognosis associated with CMV infection is poor. In particular, CMV pneumonia is frequent and severe in transplant patients with a mortality rate of 50-70%.

Antiviral drugs have improved the survival and quality of life of immunocompromised individuals suffering from CMV infection or reactivation. They are administered as prophylaxis, pre-emptive therapy (i.e., prior to the onset of clinical symptoms), or as directed therapy for the active disease. Drugs currently approved for clinical use in treating CMV include ganciclovir (or its prodrug valganciclovir), foscarnet, cidofovir, fomivirsen and more recently letermovir. Unfortunately, however, many antiviral agents exhibit undesirable side effects such as myelosuppression and nephrotoxicity. Furthermore, in many instances, patients are unresponsive to CMV therapies and the infection progresses leading to significant morbidity and mortality.

Accordingly, there is an ongoing need to develop novel antiviral treatments with improved side effect profiles and clinical effectiveness to reduce infection following transplantation or immunosuppression.

SUMMARY OF THE INVENTION

This invention is predicated, in part, on the inventors' finding that anti-CMV antibodies produced by the humoral immune response are sufficient to inhibit or prevent CMV reactivation prior to the generation of antigen-specific T cell responses. This finding has been reduced to practice in a method for inhibiting the reactivation of CMV in immunocompromised mammals (i.e., a mammal receiving a bone-marrow or hematopoietic stem cell transplant).

Accordingly, in one aspect, the present invention provides a method for inhibiting CMV reactivation in a transplant recipient with a CMV-seropositive serological status, the method comprising obtaining serum and/or plasma from the transplant recipient prior to transplantation and administering an effective amount of the serum and/or plasma, or a component thereof, to the transplant recipient before, concomitant with or after, transplantation, wherein the serum or plasma comprises one or more anti-CMV antibodies.

In another aspect, the present invention provides a method for inhibiting CMV reactivation in a subject with a CMV-seropositive serological status following the administration of an immunosuppressive agent, the method comprising obtaining serum and/or plasma from the subject prior to administration of the immunosuppressive agent and administering an effective amount of the serum and/or plasma, or a component thereof, to the subject before, concomitant with or after, administration of the immunosuppressive agent, wherein the serum or plasma comprises one or more anti-CMV antibodies.

In another aspect, the present invention provides a method for preventing CMV infection in a transplant recipient, wherein the transplant donor has a CMV-seropositive serological status, the method comprising obtaining serum and/or plasma from the transplant donor and administering an effective amount of the serum and/or plasma, or a component thereof, to the transplant recipient before, concomitant with or after, transplantation, wherein the serum or plasma comprises one or more anti-CMV antibodies.

In another aspect, the present invention provides a method for inhibiting viral spread in a transplant recipient with a CMV-seropositive serological status, the method comprising obtaining serum and/or plasma from the transplant recipient prior to transplantation and administering an effective amount of the serum and/or plasma, or a component thereof, to the transplant recipient before, concomitant with or after, transplantation, wherein the serum or plasma comprises one or more anti-CMV antibodies.

In another aspect, the present invention provides a method for inhibiting viral spread in a transplant recipient with a CMV-seronegative serological status, wherein the transplant donor has a CMV-seropositive serological status, the method comprising obtaining serum and/or plasma from the transplant donor and administering an effective amount of the serum and/or plasma, or a component thereof, to the transplant recipient before, concomitant with or after, transplantation, wherein the serum or plasma comprises one or more anti-CMV antibodies.

In an embodiment, the anti-CMV antibodies are specific for CMV strains present in the CMV-seropositive subject, CMV-seropositive transplant recipient and/or CMV-seropositive transplant donor.

BRIEF DESCRIPTION OF THE DRAWINGS

Embodiments of the disclosure are described herein, by way of non-limiting example only, with reference to the accompanying drawings.

DETAILED DESCRIPTION OF THE INVENTION

Figure 1:
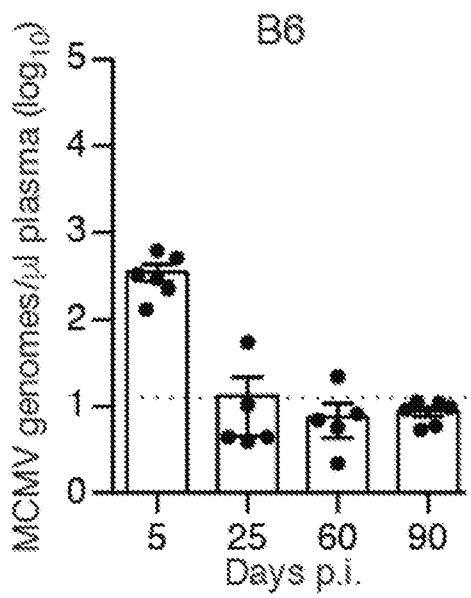
FIG. 1 is a graphical representation showing that murine CMV (MCMV) reactivation is dependent on GVHD. (A) C57BL6/J (B6) mice were infected with MCMV and the presence virus in the plasma was quantified by qPCR (number of MCMV genomes/μL plasma ($\log_{10}$); y-axis) at the indicated times post-injection (days; x-axis) (n=6). (B-F) Latently infected B6 mice (>90 days pi) were lethally irradiated and transplanted with T cell depleted (TCD) BM (non-GVHD) or BM+T cells (GVHD) from naïve BALB/c mice. (B) Mice with GVHD have a significantly poorer survival outcome than non-GVHD mice. Survival outcome (Kaplan-Meier analysis compared by log-rank analysis). Combined data from 2 experiments (non-GVHD group, n=7; GVHD group, n=11). Mice were monitored weekly for (C) GVHD clinical score and (D) MCMV viremia. (E) Viremia for individual mice at 4 weeks post-transplant is plotted. Data combined from 3 experiments (non-GVHD group, n=12; GVHD group, n=17). (F) Viral titres were determined in the indicated target organ by plaque assay at week 4-5 post-transplant. Data combined from 3 experiments (non-GVHD group, n=12; GVHD group, n=13). (G) The presence of virus in the plasma of BALB/c mice was monitored by qPCR at the indicated times post-infection (p.i.). (H-I) Latently infected BALB/c mice (>90 days pi) were lethally irradiated and transplanted with either T cell depleted BM (non-GVHD) or BM+ cells (GVHD) from naïve B6 mice. (H) 5 weeks post-transplant MCMV viremia in the plasma was quantified by PCR (non-GVHD group, n=14; GVHD group, n=15) and (I) MCMV titres in target organs were measured by plaque assay (non-GVHD group, n=8; GVHD group, n=10). Unless otherwise noted data is presented as mean±SEM. *$p<0.05$, $p<0.01$, *$p<0.001$, ****$p<0.0001$ (Mann-Whitney U test). Dotted line represents limit of detection.
Figure 1:
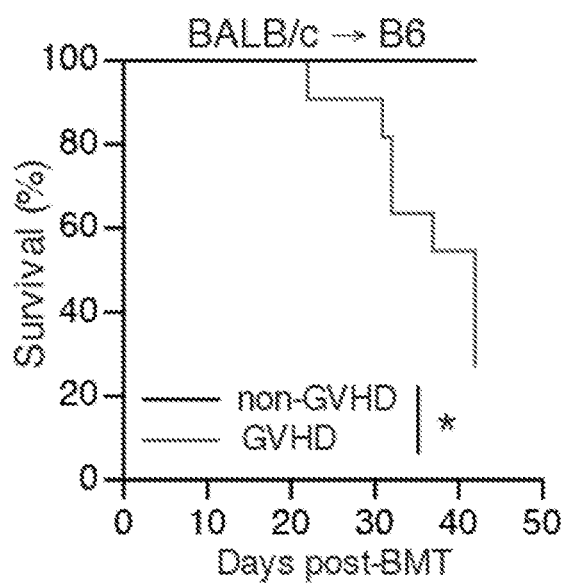
Figure 1:
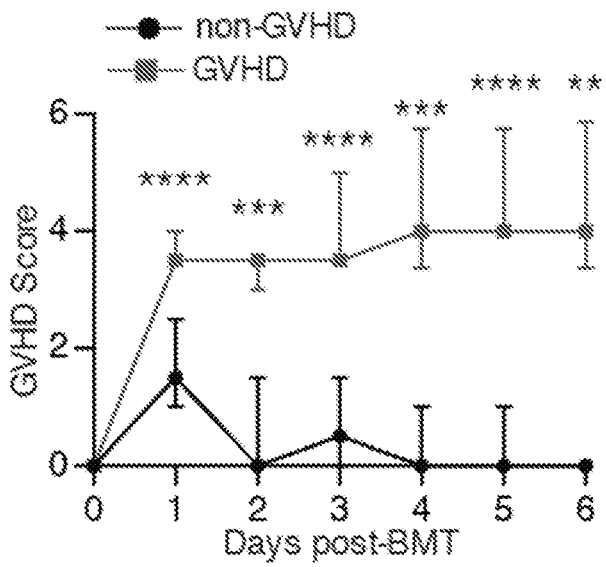
Figure 1:
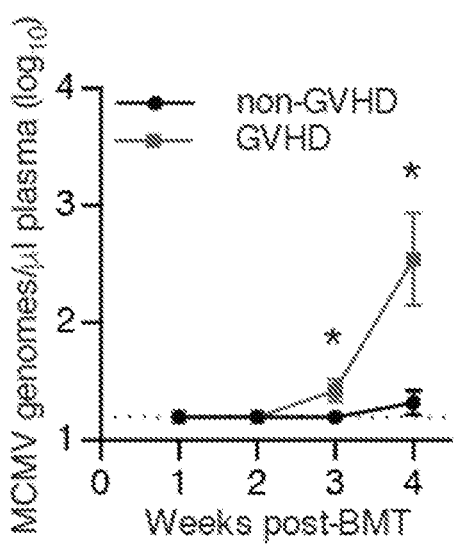
Figure 1:
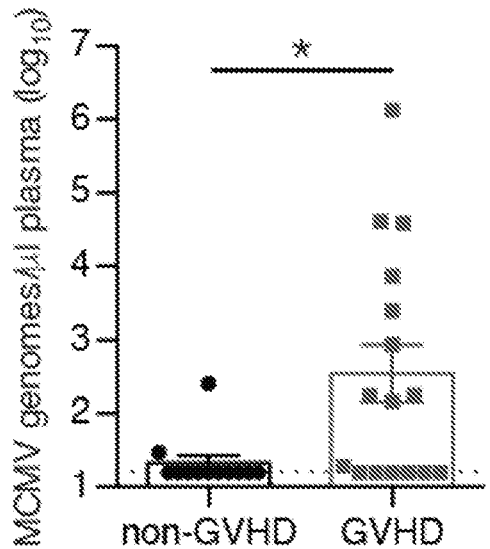
Figure 1:
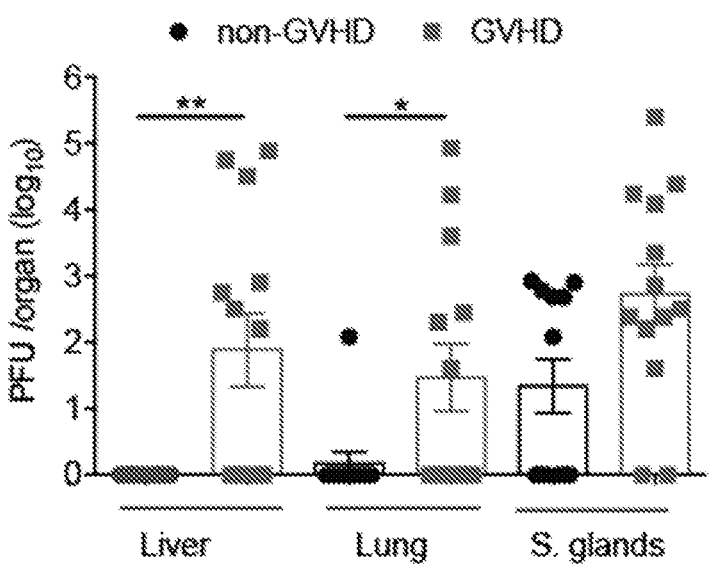
Figure 1:
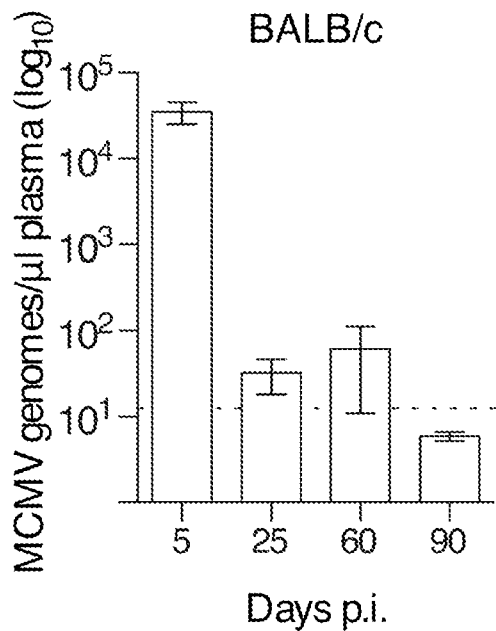
Figure 1:
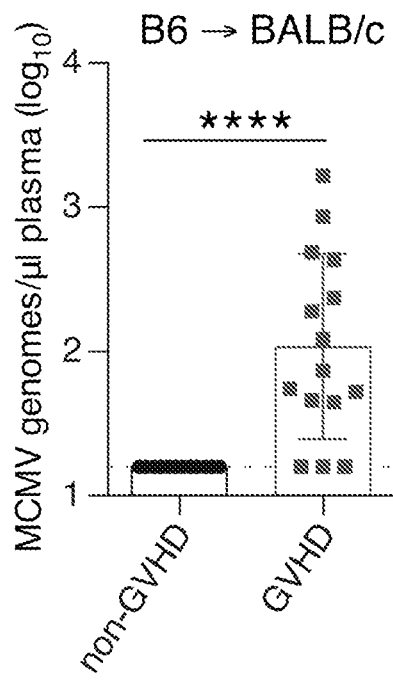
Figure 1:
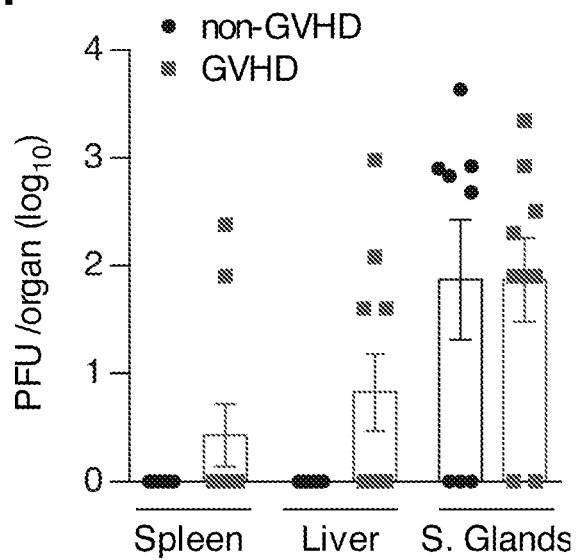

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it is understood that such identifiers can change and particular information on the internet can come and go, but equivalent information can be found by searching the internet. Reference to the identifier evidences the availability and public dissemination of such information.

The articles "a", "an" and "the" include plural aspects unless the context clearly dictates otherwise. Thus, for example, reference to "an agent" includes a single agent, as well as two or more agents; reference to "a treatment" includes a single treatment, as well as two or more treatments; and so forth.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, the term "agent" includes a compound that induces a desired pharmacological and/or physiological effect. The term also encompasses pharmaceutically acceptable and pharmacologically active ingredients of those compounds specifically mentioned herein including but not limited to salts, esters, amides, prodrugs, active metabolites, analogs and the like. When the above term is used, it will be understood by persons skilled in the art that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" also includes a cell which is capable of producing and secreting the agents referred to herein, as well as a polynucleotide comprising a nucleotide sequence that encode such agents. Thus, the term "agent" extends to nucleic acid constructs including vectors such as viral or non-viral vectors, expression vectors and plasmids for expression in and secretion in a range of cells.

The term "subject" as used herein refers to mammals and includes humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Typically, the mammal is human, laboratory test animal or companion animal. More typically, the mammal is a human.

As used herein the term "effective amount" includes within its meaning a non-toxic but sufficient amount of serum and/or plasma, or a component thereof, which is effective for inhibiting CMV reactivation or for treating or preventing CMV infection. The exact amount required will vary from subject to subject depending on factors such as the subject being treated, the age and general health and well-being of the subject and the mode of administration and so forth. Thus, it is not possible to specify an exact "effective amount". However, for any given case, an appropriate "effective amount" may be determined by one of ordinary skill in the art using only routine experimentation.

As used herein the terms "treating", "treatment", and the like refer to any and all methods which remedy, prevent, hinder, retard, ameliorate, reduce, delay or reverse the progression of CMV infection or one or more undesirable symptoms thereof in any way. Thus the terms "treating" and the like are to be considered in their broadest context. For example, treatment does not necessarily imply that a patient is treated until total recovery. CMV infection is typically characterized by multiple symptoms, and thus the treatment need not necessarily remedy, prevent, hinder, retard, ameliorate, reduce, delay or reverse all of said symptoms. Methods of the present disclosure may involve "treating" the CMV infection in terms of reducing or ameliorating the occurrence of a highly undesirable event or symptom associated with the CMV infection or an outcome of the progression of the infection, but may not of itself prevent the initial occurrence of the event, symptom or outcome. Accordingly, treatment includes amelioration of the symptoms of CMV infection or preventing or otherwise reducing the risk of developing symptoms of CMV infection.

In the context of the present disclosure, the terms "inhibiting" and variations thereof such as "inhibition" and "inhibits" do not necessarily imply the complete inhibition of the specified event, activity or function. Rather, the inhibition may be to an extent, and/or for a time, sufficient to produce the desired effect. Inhibition may be prevention, retardation, reduction or otherwise hindrance of the event, activity or function. Such inhibition may be in magnitude and/or be temporal in nature. In particular contexts, the terms "inhibit" and "prevent", and variations thereof may be used interchangeably.

Inhibition of CMV Reactivation

The present disclosure describes the inhibition of CMV reactivation in CMV-seropositive transplant recipients, which is predicated on the finding that antibodies produced by the humoral immune response are sufficient to inhibit or prevent CMV reactivation. Accordingly, provided herein are methods for inhibiting CMV reactivation in a CMV-seropositive transplant recipient by administering serum and/or plasma from the transplant recipient, wherein the serum or plasma comprises one or more anti-CMV antibodies that are specific for the CMV strains present in the transplant recipient. The disclosure also provides methods for inhibiting or preventing CMV reactivation in CMV-seropositive donor organs, tissues or cells by administering serum and/or plasma from the transplant donor to the transplant recipient, wherein the serum or plasma comprises one or more anti-CMV antibodies that are specific for the CMV strains present in the donor organs, tissues or cells.

Accordingly, provided herein are methods for inhibiting CMV reactivation in a CMV-seropositive transplant recipient, the method comprising obtaining serum and/or plasma from the transplant recipient prior to transplantation and administering an effective amount of the serum and/or plasma, or a component thereof, to the transplant recipient before, concomitant with or after, transplantation, wherein the serum or plasma comprises one or more anti-CMV antibodies.

The term "CMV reactivation" as used herein refers to the reactivation of a latent CMV infection. CMV reactivation can result from a number of different stimuli, including immunosuppression and inflammation. For example, CMV reactivation can occur following transplantation.

The term "CMV serological status" as used herein refers to the presence or absence of CMV protein or nucleic acid in a blood sample. The term "CMV-seropositive" is used to refer to a transplant recipient, transplant donor, or other subject with antibodies to CMV or CMV protein or nucleic acid present in their blood, which is indicative of a latent CMV infection. The term "CMV-seronegative" is used to refer to a transplant recipient, transplant donor, or other subject without antibodies to CMV or CMV protein or nucleic acid present in their blood, which is indicative of the absence of a latent CMV infection.

The skilled person will appreciate that the determination of CMV serological status in accordance with the present disclosure may be performed using a variety of techniques known in the art. In exemplary embodiments, CMV serological status may be determined by detecting antibodies to CMV or CMV protein or nucleic acid in a blood sample. In an embodiment, polymerase chain reaction (PCR)-based methods can be used to detect CMV nucleic acids. In another embodiment, CMV serological status may be determined by detecting anti-CMV antibodies. Suitable methods for the detection of anti-CMV antibodies include enzyme-linked immunosorbent assay (ELISA), radioimmunoassay (RIA), western blotting and immunohistochemistry.

In an exemplary embodiment, the methods described herein comprise the determination of the CMV serological status of the transplant recipient, transplant donor or other subject. Alternatively, the CMV serological status may be known. Determination of CMV serological status is routinely made in, for example, young adults, pregnant women or immune-compromised subjects with flu-like symptoms.

The terms "transplant" or "graft" mean refers to an organ, tissue or cell that has been transplanted from one subject to a different subject, or transplanted within the same subject (e.g., to a different area within the subject). Organs such as liver, kidney, heart or lung, or other body parts, such as bone or skeletal matrix such as bone marrow, tissue, such as skin, cornea, intestines, endocrine glands, or stem cells or various types, or hematopoietic cells including hematopoietic stem and progenitor cells, are all examples of transplants. The graft or transplant can be an allograft, autograft, isograft, or xenograft. The term "allograft" refers to a graft between two genetically non-identical members of a species. The term "autograft" refers to a graft from one area to another on a single individual. The term "isograft" or "syngraft" refers to a graft between two genetically identical individuals. The term "xenograft" refers to a graft between members of different species.

In exemplary embodiments, the transplant may be a solid organ transplant, a bone-marrow transplant or a hematopoietic stem cell transplant.

In particular embodiments of the present disclosure, the serum and/or plasma of CMV-seropositive transplant recipients are administered before, concomitant with or after transplantation to inhibit CMV reactivation.

The skilled person will appreciate that serum is a heterogeneous mixture of components, including but not limited to electrolytes, antibodies, antigens, hormones and any exogenous substances (e.g., drugs and microorganisms). In an exemplary embodiment, an effective amount of serum is administered to a transplant recipient before, concomitant with, or after transplantation.

Similarly, the skilled person would also appreciate that plasma is a heterogeneous mixture of components including but not limited to proteins (e.g., serum albumins, globulins and fibrinogen), glucose, clotting factors, electrolytes, hormones, carbon dioxide and oxygen. Plasma differs from serums in that it contains fibrinogen and clotting factors. In an exemplary embodiment, an effective amount of plasma is administered to a transplant recipient before, concomitant with, or after transplantation.

In an exemplary embodiment, an effective amount of a component of serum or plasma is administered to a transplant recipient before, concomitant with, or after transplantation. Suitable components include an isolated or enriched antibody fraction and isolated anti-CMV antibodies.

The term "antibody" as used herein broadly refers to any immunoglobulin (Ig) molecule comprised of four polypeptide chains, two heavy (H) chains and two light (L) chains, or any functional fragment, mutant, variant, or derivation thereof, which retains the essential epitope features of an Ig molecule. Such mutant, variant, or derivative antibody formats are known in the art.

In a full size antibody, each heavy chain comprises a heavy chain variable region (HCVR or VH) and a heavy chain constant region. The heavy chain constant region is comprised of three domains, CH1, CH2 and CH3. Each light chain comprises a light chain variable region (LCVR or VL) and a light chain constant region, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3 and FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The skilled person will appreciate that isolation or enrichment of the antibody fraction of serum or plasma will increase the ratio of antibodies present relative to other serum or plasma components. This is not limited to a particular antibody species. Thus, the isolated or enriched antibody fraction will comprise antibodies with specificity to a broad range of different viral antigens, including for example, antigens from other viruses such as adenovirus, Epstein-Barr virus and BK virus. In an exemplary embodiment, the component is isolated anti-CMV antibodies. The skilled person will appreciate that isolated anti-CMV antibodies will exhibit specificity to a diverse range of CMV species and antigens and may be of any type, class or subclass. In an exemplary embodiment, the isolated anti-CMV antibodies are IgG$^{CMV}$ antibodies.

The term "cytomegalovirus" or "CMV" is not intended to be limited to a particular CMV strain or species. The extent of strain diversity in single CMV-seropositive individuals has been previously shown (e.g., Novak et al., (2008), *Journal of Clinical Microbiology*, 46(3): 882-886; Binder et al., (1999), *Journal of Virological Methods*, 78153-78162; Coaquette et al., (2004), *Clinical Infection and Disease*, 39155-39161; and Rasmussen et al., (1997), *Journal of Infection and Disease*, 175179-175184). Accordingly, the skilled person would appreciate that CMV-seropositive transplant recipients, transplant donors or other subjects contemplated by the present disclosure may be infected with multiple strains of CMV.

In particular embodiments of the present disclosure, the serum or plasma, or a component thereof comprises anti-CMV antibodies with specificity to two or more CMV antigens. The use of multiple antigens is a preferred method for the inhibition of CMV reactivation as a single antigen directed antibody is unlikely to provide broad protection for the diverse range of CMV strains that are present in CMV-seropositive transplant recipients, transplant donors or other subjects contemplated by the present disclosure.

The present disclosure also provides a method for inhibiting CMV reactivation in CMV-seropositive subjects in other contexts of immunosuppression. For example, provided herein is a method for inhibiting CMV reactivation in a CMV-seropositive subject following the administration of an immunosuppressive agent, the method comprising obtaining serum and/or plasma from the subject prior to administration of the immunosuppressive agent and administering an effective amount of the serum and/or plasma, or a component thereof, to the subject before, concomitant with or after administration of the immunosuppressive agent, wherein the serum or plasma comprises one or more anti-CMV antibodies.

Exemplary "immunosuppressive agents" that may be employed in accordance with the present disclosure include, but are not limited to corticosteroids (e.g., prednisone, prednisolone, fludarabine, budesonide and alemtuzumab), calcineurin inhibitors (e.g., cyclosporine and tacrolimus), mTOR inhibitors (e.g., sirolimus, everolimus and rapamycin) and IMDH inhibitors (e.g., azathioprine, leflunomide and mycophenolate).

In an exemplary embodiment, the subject is a transplant recipient. Immunosuppression in transplant recipients is multifactorial and immunosuppression may result from the recipient's primary disease, or from the preparatory regimen. Alternatively, immunosuppression in transplant recipients can also arise from GVHD or from the treatment of GVHD. Accordingly, in an exemplary embodiment, the subject has GVHD.

The administration of immunosuppressive agents is also common in the treatment of immune or autoimmune disorders. The term "immune or autoimmune disorder" includes, but is not limited to type I diabetes, rheumatoid arthritis, systemic lupus erythematosus (SLE), multiple sclerosis, myasthenia gravis, Sjogren's syndrome or acquired immunodeficiency syndrome (AIDS).

In an exemplary embodiment, the subject has immune-related adverse events (irARs) following treatment with a checkpoint inhibitor. It has been shown that CMV reactivation occurs in patients with checkpoint-inhibitor induced irARs, such as immune-related diarrhoea and colitis (Franklin et al., (2017), *European Journal of Cancer*, 86: 248-256). The term "checkpoint inhibitor" as used herein refers to any agent that inhibits immune checkpoints. Examples of checkpoint inhibitors include, but are not limited to, anti-CTLA-4 antibodies (e.g., ipilimumab), anti-PD-1 antibodies (e.g., nivolumab and pembrolizumab) and combinations thereof.

Inhibition of Viral Spread

The present disclosure describes the inhibition of CMV viral spread in CMV-seropositive transplant recipients by administering serum and/or plasma from the transplant recipient, wherein the serum or plasma comprises one or more anti-CMV antibodies. The disclosure also provides methods for inhibiting or preventing CMV viral spread in CMV-seropositive donor organs, tissues or cells by administering serum and/or plasma from the transplant donor to the transplant recipient, wherein the serum or plasma comprises one or more anti-CMV antibodies.

The term "viral spread" as used herein refers to the cell-to-cell transmission and cell-free transmission of virus within a host. Accordingly, skilled persons would appreciate that viral spread may occur within a host (i.e., transplant recipient) following reactivation of a latent CMV infection, or from donor organs, tissue or cells derived from a CMV-seropositive donor that is transmitted to other cells in a CMV-seropositive or CMV-seronegative transplant recipient following transplantation.

Treatment or Prophylaxis

The findings described herein offer novel opportunities for the treatment or prevention of CMV infection following transplantation, where the transplant recipient and/or transplant donor are CMV-seropositive.

Accordingly, embodiments of the present disclosure provide methods for treating or preventing CMV infection in a CMV-seropositive transplant recipient, the method comprising obtaining serum and/or plasma from the transplant recipient prior to transplantation and administering an effective amount of the serum and/or plasma, or a component thereof, to the transplant recipient before, concomitant with or after transplantation, wherein the serum or plasma comprises one or more anti-CMV antibodies.

In another embodiment, the present disclosure provides methods for preventing CMV infection in a transplant recipient with a CMV-seronegative serological status, wherein the transplant donor has a CMV-seropositive serological status, the method comprising obtaining serum and/or plasma from the transplant donor prior to transplantation and administering an effective amount of the serum and/or plasma, or a component thereof, to the transplant recipient before, concomitant with or after transplantation, wherein the serum or plasma comprises one or more anti-CMV antibodies.

The skilled person will appreciate that the transplant donor may be CMV-seropositive. The CMV-seropositive transplant donor will have unique range of anti-CMV antibodies that that may be distinct from the transplant recipient or the transplant recipient may be CMV-seronegative. Thus, the method for inhibiting CMV reactivation in accordance with the present disclosure may or may not require the administration of serum and/or plasma from the transplant donor to treat or prevent a CMV infection arising from the transplanted cells or tissue.

In exemplary embodiments, the method for treating or preventing CMV infection in a CMV-seropositive transplant recipient described hereinbefore further comprises obtaining serum and/or plasma from the CMV-seropositive transplant donor and administering an effective amount of the donor serum and/or plasma, to the transplant recipient before, concomitant with or after transplantation.

Also provided herein is a method for treating or preventing CMV infection in a transplant recipient, wherein the transplant donor is CMV-seropositive, the method comprising obtaining serum and/or plasma from the transplant donor and administering an effective amount of the serum and/or plasma, or a component thereof, to the transplant recipient before, concomitant with or after transplantation, wherein the serum or plasma comprises one or more anti-CMV antibodies.

Administration

The serum or plasma, or a component thereof, according to the present disclosure may be administered to the transplant recipient before, concomitant with or after transplantation. One skilled in the art would be able to determine the time of administration to treat, prevent or prime the transplant recipient for transplantation. Furthermore, the one skilled in the art would be able, by routine experimentation, to determine an effective, non-toxic amount to be employed, taking into consideration the time of administration; the route of administration; the rate of sequestration; the duration of the treatment; other agents used in combination or coincidental with the treatment, together with other related factors well known in medicine.

Those skilled in the art will appreciate that the methods of the present disclosure may also be employed in combination with other therapies and treatments. For example, CMV-seropositive serum and/or plasma, or a component thereof, may be administered in combination with an adoptive cell transfer treatment (e.g., adoptive transfer of CMV-specific T cells or transplant donor-derived B cells), intravenous CMV immunoglobulin (e.g., CytoGam) or additional antiviral agents (e.g., ganciclovir, valganciclovir, foscarnet, cidofovif and formivirsen). For combination therapies, each component of the combination may be administered at the same time, or sequentially in any order, or at different times, so as to provide the desired effect. When administered separately, it may be preferred for the components to be administered by the same route of administration, although it is not necessary for this to be so. Alternatively, the components may be formulated together in a single dosage unit as a combination product.

Typically, antiviral agents and immunosuppressive agents are provided in the form of pharmaceutical compositions with one or more pharmaceutically acceptable carriers. The compositions can also comprise additional ingredients such as diluents, stabilizers, excipients, and adjuvants.

Depending on factors including the route of administration, the carriers, diluents and adjuvants can include buffers such as phosphate, citrate, or other organic acids; antioxidants such as ascorbic acid; proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween™, Pluronics™ or polyethylene glycol (PEG). Compositions may be administered in any suitable dosage form and by any suitable route. For example, administration may be systemic, regional or local and may be, for example, oral, nasal, oromucosal, topical, intracerebral, intrathecal, intracranial, epidural, intravenous, intramuscular, or subcutaneous. Compositions can be administrated as a single dose or multiple doses, and at varying intervals.

All publications mentioned in this specification are herein incorporated by reference. The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the present disclosure without departing from the spirit or scope of the disclosure as broadly described. The present embodiments are, therefore, to be considered in all respects as illustrative and not restrictive.

The present disclosure will now be further described in greater detail by reference to the following specific examples, which should not be construed as in any way limiting the scope of the disclosure.

EXAMPLES

Materials and Methods

Mice

Non-infected female mice aged between 8-12 weeks were used as donors in the transplant protocols and for primary infection of MCMV (to establish latency). Seropositive (latently-infected) and age-matched seronegative (non-infected) female mice were 19-25 weeks of age. BALB/c weaners were used at 3 weeks of age.

Strains utilised in experiments are listed in Table 1. Mice were housed in micro-isolator cages under a 12:12-h light-dark cycle and were provided with a standard mouse diet and autoclaved acidified water (pH 2.5). All animal experimentation was performed according to the guidelines and with the approval of the Animal Ethics Committees of QIMR Berghofer Medical Research Institute and the University of Western Australia.

TABLE 1

Mouse strains

| Strain | Abbreviation | Source |
| --- | --- | --- |
| C57BL/6 | B6 | Animal Resources Centre (Perth, WA, Australia) |
| B6.Ptprc$^a$ | PTP | Animal Resources Centre (Perth, WA, Australia) |
| B6D2F1 | B6D2F1 | Animal Resources Centre (Perth, WA, Australia) |
| C3H.SW | C3H.SW | Jackson Laboratories (Bar Harbor, Main, USA) |
| B6.IFNAR1$^{-/-}$ | B6.IFNAR KO | Jackson Laboratories (Bar Harbor, Main, USA) |
| B6.IFN gamma $^{-/-}$ | B6.IFNγ KO | Jackson Laboratories (Bar Harbor, Main, USA) |
| BALB/c.IFN gamma $^{-/-}$ | BALB. IFNγ KO | Jackson Laboratories (Bar Harbor, Main, USA) |
| B6.PtpxC57BL/6j | PTPxC57 | Bred-in-house at QIMR Berghofer facility (Brisbane, QLD, Australia) |
| BALB/c | BALB/c | Animal Resources Centre (Perth, WA, Australia) |
| BALB.B6-CT6 | CT6 | Bred in-house at Animal Services Facility of the University of Western Australia (Perth, WA, Australia) |
| B6. μMt $^{-/-}$ | μMt KO | Bred-in-house at QIMR Berghofer facility (Brisbane, QLD, Australia) |
| B6.TCRδ-/- | | Bred-in-house at QIMR Berghofer facility (Brisbane, QLD, Australia) |
| B6.FcγIII-/- | | Bred-in-house at QIMR Berghofer facility (Brisbane, QLD, Australia) |

General Reagents

Media and Solutions

RPMI Media

RPMI-1640 (Roswell Park Memorial Institute—1640) (Gibco)+2% heat inactivated fetal bovine serum (FBS) (Life Technologies), 1% penicillin/streptomycin (Sigma-Aldrich) and 2 mM L-glutamine (Life Technologies). The solution was filter sterilized (0.22 μm) and stored at 4° C.

Serum-Free RPMI Media (No FBS)

RPMI-1640 (Roswell Park Memorial Institute—1640) (Gibco)+1% penicillin/streptomycin (Sigma-Aldrich) and 2 mM L-glutamine (Life Technologies). The solution was filter sterilized (0.22 μm) and stored at 4° C.

IMDM Complete

IMDM (Life Technologies), 10% FBS, 1% penicillin/streptomycin (Sigma-Aldrich), 2 mM L-glutamine (Hyclone Thermo Scientific), 1% non-essential amino acids (Life Technologies), 1 mM sodium pyruvate (Sigma-Aldrich) and 0.05 mM 2-mercaptoethanol (Sigma-Aldrich). The solution was filter sterilized (0.22 μm) and stored at 4° C.

PBS 145 mM NaCl (Univar, AR), 10 mM $Na_2HPO_4$ (Univar, AR) and 3 mM $KH_2PO_4$ (Univar, AR).

FACS Buffer

PBS, 2% FBS (Life Technologies), 5 mM EDTA (Chem-Supply)

Gey's Buffer 7 g/L $NH_4Cl$ (Sigma-Aldrich), 0.37 g/L KCl (Sigma-Aldrich), 0.3 g/L $Na_2HPO_4·12H_2O$ (Sigma-Aldrich), 0.024 g/L $KH_2PO_4$ (Sigma-Aldrich), 1 g/L glucose (Sigma-Aldrich), 0.01 g/L phenol red (Sigma-Aldrich), 0.021 g/L $MgCl_2·6H_2O$ (Sigma-Aldrich), 0.07 g/L $MgSO_4·7H_2O$ (Sigma-Aldrich), 0.017 g/L $CaCl_2$ (Sigma-Aldrich) and 1.125 g/L $NaHCO_3$ (Sigma-Aldrich).

Mouse Cytomegalovirus Latency Model

Mice were inoculated intraperitoneally (i.p.) with $1×10^4$ plaque-forming units (PFU) of salivary gland-propagated MCMV-K181Perth or MCMV-K181Perth-LacZ as indicated. BALB/c and DBA2 mice received $5×10^3$ PFU due to asplenia with higher doses. All mice were housed for at least 3 months prior to transplant, to allow latent infection to develop. Latently infected mice were then used as recipients for BMT.

Bone Marrow Transplantation

Bone Marrow Harvest and Processing

The hind legs were removed and the bones scraped clean of tissue. Bone marrow (BM) was flushed, using RPMI media from femurs, tibiae and pelvises with a 26-gauge needle and syringe, with the resulting cell suspension filtered through a 70 μm cell strainer (Miltenyi, Australia), washed with RPMI media and an aliquot counted on an AcT Diff Coulter Counter (Beckman Coulter, Australia).

T cell depleted (TCD) bone marrow was obtained by incubating BM with an antibody master mix, produced in-house, containing anti-CD4 (RL172.4), anti-CD8 (TIB 211) and CD90.2 (HO-13-4) at 30 ml antibody master mix per $350×10^6$ BM cells, for 30 minutes on ice. Cells were washed twice with RPMI media (without FBS) and then incubated with 1.3 ml rabbit complement (Cedarlane Laboratories, Burlington, ON, Canada) per $100×10^6$ cells for 40 minutes at 37° C. Cells were subsequently washed twice with RPMI media (without FBS) and then resuspended in RPMI media. An aliquot was removed for counting and purity analysis by FACS (BD LSR Fortessa) to ensure less than 1% viable $CD3^+$ T cells remained.

T Cell Isolation and Selection

Splenocytes were isolated by mashing spleens in RPMI media and the cell suspension filtered through a 70 μm cell strainer. Red blood cells (RBCs) were lysed using 1 mL of Gey's buffer per spleen, for 1 minute. Lysis was ceased by washing twice with RPMI media and centrifugation at 450 g for 5 minutes. Cells were resuspended in RPMI media and an aliquot removed for counting using an AcT Diff Coulter Counter (Beckman Coulter, Australia).

For whole $CD3^+$ T cell selection, cells were incubated with antibody master mix containing in-house produced monoclonal antibody (mAb) supernatants against CD19, B220, GR1, Ter119 and CD11b, each at 10 µg per 100×10⁶ cells each, for 20 minutes on ice. Cells were washed with FACS buffer and incubated with pre-washed Biomag goat anti-rat IgG beads (Qiagen, VIC, Australia) at 20 µL beads per 1×10⁶ cells, for 20 minutes on ice with occasional mixing. The cell suspension was placed on a magnetic stand for 3-5 minutes, until clear. The clear supernatant was collected and an aliquot removed for counting and to determine purity by FACS to ensure >80% CD3⁺ selection. For selection of purified CD4⁺ or CD8⁺ T cells from splenocytes, cells were positively selected using the MACS system (Miltenyi Biotec, Bergisch Gladbach, Germany). Purified CD4⁺ T cells (>80% CD4⁺CD3⁺, ≤0.8% CD8⁺CD3⁺) or CD8⁺ T cells (>80% CD8⁺CD3⁺, <1.2% CD4⁺CD3⁺), cells were selected according to the manufacturer's protocol.

Transplantation

Latently infected recipient mice received total body irradiation (TBI) prior to transplantation (day −1), split into 2 doses separated by 3 hours (Table 2) from a Gammacell® caesium source gamma irradiator.

TCD BM cells alone (to mimic non-GVHD conditions) or BM+T cells (to induce GVHD) were resuspended in Leibovitz's L-15 Medium (Sigma Aldrich) and injected intravenously into the tail vein of mice with a 27 G insulin syringe (BD Biosciences, Australia) (Table 2). Mice were monitored daily and scored weekly for signs of GVHD according to clinical parameters: weight loss, posture (hunching), mobility, fur texture and skin integrity (Table 3; Cooke et al., (1996), *Blood,* 88: 3230-3239). Each parameter was graded with a maximum of 2, and once the animal reached a cumulative score of 6, was sacrificed and counted as death due to GVHD.

Serum Transfer

Protection of BALB/c weaners from MCMV infection was tested by i.p. injection of serum. Serum was collected from (i) non-GVHD and GVHD mice at day 14 and day 28 post-transplant or (ii) mice latently infected with either K181 or the N1 MCMV isolate. Weaners were injected with relevant MCMV isolates 24 hr after serum transfer and viral replication quantified 4 days p.i. BMT recipients were injected with serum from latently infected (seropositive) or uninfected (seronegative) BALB/c mice, twice weekly post-transplant commencing at day 14. Mice received a total volume of 1000 µl of serum (5×200 µl). Serum was collected from BALB/c mice infected with 5×10³ PFU of MCMV-K181, or the N1 MCMV strain, at least 60 days p.i. A pooled sera preparation was generated by combining an equal volume of serum isolated from mice individually infected with one of eight MCMV isolates: K181, N1, G4, G5, K4, K6, GIF or M16A (Voigt, et al. (2003), *Proceedings of the National Academy of Sciences USA,* 100: 13483-13488). All sera were UV-inactivated prior to injection to ensure viable MCMV was not transferred. Titration of serum on permissive cell monolayers confirmed the absence of viable virus. BMT recipients were injected with K181, N1 or pooled sera, twice weekly post-transplant commencing at day +14. Mice received a total volume of 800 µl of serum (4×200 µl).

MCMV Latently Infected Bone Marrow Chimeras

Recipient mice were irradiated (1000 cGy) and transplanted with 10×10⁶ BM cells.

The following combination of donor/recipients was transplanted:
PTP→B6; IFNγ KO→PTP; PTP→IFNγ KO; and IFNγ KO→IFNγ KO
(PTP—CD45.1⁺; B6—CD45.2⁺; and IFNγ KO—CD45.2⁺)

Mice were allowed to reconstitute for 2 months prior to MCMV infection of 1×10⁴ PFU of K181-MCMV-Perth and allowed to enter latency for 3 months prior to secondary transplantation.

TABLE 2

Characteristics of the mouse stem cell transplant systems

| Transplant system | Haplotype | Irradiation dose [cGy] | BM cells | T cells |
|---|---|---|---|---|
| BALB/c → B6 | H-2$^d$ → H-2$^b$ | 1000 | 10 × 10⁶ | 2 × 10⁶ CD4⁺ 2 × 10⁶ CD8⁺ |
| B6 → BALB/c | H-2$^b$ → H-2$^d$ | 900 | 5 × 10⁶ | 0.2 × 10⁶ CD3⁺ |
| BALB/c → DBA2 | H-2$^d$ → H-2$^d$ | 900 | 5 × 10⁶ | 2 × 10⁶ CD3⁺ |
| B6 → B6D2F1 | H-2$^b$ → H-2$^{b/d}$ | 1100 | 5 × 10⁶ | 3 × 10⁶ CD3⁺ |
| C3H.SW → B6 | H-2$^b$ → H-2$^b$ | 1000 | 10 × 10⁶ | 2 × 10⁶ CD8⁺ |

TABLE 3

Scoring matrix utilised to determine development of GVHD

| Criteria | Score 0 | Score 0.5 | Score 1 | Score 1.5 | Score 2 |
|---|---|---|---|---|---|
| Skin integrity | Normal | Minor scaling of paws OR tail OR ears only | Scaling of paws/tail | Areas of hair loss with skin thickening | Obvious areas of denuded skin |
| Posture | Normal | Very minor hunching at rest only | Clear hunching noted only at rest | Hunching also noted with movement | Severe hunching impairs movement |
| Fur texture | Normal | Minor ruffling (partial and over ventral surface only) | Mild to moderate ruffling (ruffling over ventral surface) | Moderately severe ruffling (complete ruffling over ventral surface and partial over dorsal surface) | Severe ruffling, poor grooming (complete over ventral and dorsal surface) |
| Activity | Normal | Minor decrease only | Mild to moderately decreased | Moderate to severely decreased | Stationary unless stimulated |
| Weight loss | <10% | | 10-24% | | 25% |

Depletion In-Vivo after BMT

For in-vivo depletion experiments, mice were injected intravenously with the appropriate concentration of depleting antibody in 250-350 µL saline solution (Table 4).

TABLE 4

Depleting antibodies used for in-vivo cell depletions

| Antibody target | Clone | Dose schedule* | Supplier |
|---|---|---|---|
| CD4 | GK1.5 | 500 µg/dose/mouse at day −1 250 µg/dose/mouse weekly thereafter | In-house |
| CD8 | 53-5.8 | 150 µg/dose/mouse at day −1 and weekly thereafter | In-house |
| NK1.1 | PK136 | 500 µg/dose/mouse at day −1 250 µg/dose/mouse twice weekly thereafter | In-house |

*Day 0 = day of transplant

Leukaemia Challenge

Primary leukaemia cells were generated using the expression of the human oncogene MLL-AF9 to model human AML and myeloid blast-crisis leukaemia, as previously described (Bruedigam et al., (2014), *Cell Stem Cell,* 15: 775-790). Cells were cryopreserved at disease onset, for subsequent transplantation.

Lethally-irradiated recipients were transplanted with $10 \times 10^6$ TCD BM cells and $3 \times 10^6$ CD3$^+$ purified T cells. The non-GVHD group received TCD BM only. Leukaemia cells (B6. MLL-AF9-GFP$^+$) were thawed on the day of injection and included in grafts at $1 \times 10^6$ cells per mouse. Peripheral blood was collected at 2 weeks and weekly thereafter by retro-orbital bleed into Vacuette K$_2$EDTA tubes (Greiner Bio-one) to prevent coagulation. Blood samples were counted and RBCs lysed. Survival and GVHD clinical scores were assessed weekly. Leukaemia burden in the blood was determined by enumeration of green fluorescent protein positive (GFP$^+$) cells by FACS.

For a death to be attributed to leukaemia, tumour burden in peripheral blood at either terminal or last routine bleed had to meet the following criteria to avoid overstatement of leukemic deaths when both GVHD and leukaemia were present: any limb paralysis, greater than 4% GFP$^+$ cells in peripheral blood (with any total white cell count), or present in the peripheral blood at any level but with a total white cell count $\geq 10 \times 10^6$ per mL blood.

Histological Analysis

Hematoxylin and Eosin Staining

Organs were excised and fixed in 10% formalin. Cut sections were stained with hematoxylin and eosin and analysed with a light microscope (Olympus) and images collected with a digital camera (Olympus) at the magnifications indicated.

Lac Z Staining of CMV K181-LacZ Infected Cells

Organs were excised and fixed in 2% PFA at 4° C. for 1-2 hours then transferred to 10% sucrose solution overnight at 4° C. Organs were slow-rate frozen in optimal cutting temperature (OCT) compound using a dry-ice/propanol cooling bath. Sections were cut and stained as per LacZ staining protocol (Palladino et al., (1995), *Journal of Virology,* 69: 2075-2081).

Flow Cytometry

Surface Staining

FcγRII/FcγRIII receptors were blocked with a CD32/CD16 antibody mix (generated in-house from 2.4G2 hybridoma line) to reduce non-specific antibody binding. 50 μL of 2.4G2 supernatant stock solution (5 mg/mL) was added to the cells for 10 minutes at room temperature (RT). Cells were washed in FACS buffer and surface stained. The antibodies utilized in experiments are listed in Table 5 and were used at a 1/200 dilution of the stock concentration in 100 μL final volume of FACS buffer and incubated for 20 minutes at RT.

To detect MCMV-specific T cells we used the following PE-conjugated tetramers, all purchased from ImmunoID Tetramers: H-2Ld-YPHFMPTNL MCMV—IE1, H-2Kb-SSPPMFRV MCMV-m38, H-2Db—HGIRNASFI MCMV-m45. Tetramers were used at a 1/200 dilution of the stock concentration in a 100 μL final volume FACS buffer and incubated for 30 minutes, on ice.

The fluorescence-labelled preparations were washed with FACS buffer and analysed on a LSR Fortessa II (BD Biosciences) using FACSDiva software (Version 8.0.1). Offline analysis was performed using FlowJo (Version 10, Treestar).

IE1 Peptide Stimulation and Intracellular Staining

Splenocytes were incubated with 1 μg/mL Brefeldin A (BioLegend, CA, USA) and 200 ng/mL H-2Ld MCMV-IE1-YPHFMPTNL peptide (Genscript, Piscataway, NJ, USA) in IMDM media for 4 hours at 37° C. Cells were washed and processed for surface staining as described above, followed by intracellular cytokine staining as per the manufacturer's protocol (BD Cytofix/Cytoperm Kit; BD Bioscience). Labelled cells were analysed by FACS (BD LSR Fortessa).

TABLE 5

Antibodies used for flow cytometry

| Antibody target | Clone | Conjugate | Supplier |
|---|---|---|---|
| CD3 | 145-2C11 | PE, APC | BioLegend |
| CD4 | RM4-5 | PB, PECy7 | BD Biosciences |
| | | APC | BioLegend |
| CD8 | 53-6.7 | APC, APC.Cy7 | BioLegend |
| | | FITC | Generated in-house |
| | | PerCP Cy5.5 | BD Biosciences |
| CD19 | 6D5 | APC.Cy7 | BioLegend |
| CD44 | IM7 | FITC | BioLegend |
| CD45.1 | A20 | PE, APC-Cy7 | BioLegend |
| CD45.2 | 104 | AF700, APC | BioLegend |
| CD62L | MEL14 | AF700 | BioLegend |
| CD90.2 | 23-2.1 | BV605 | BioLegend |
| CD127 | A7R34 | BV421 | BioLegend |
| CD138 | 281-2 | BV421 | BioLegend |
| IFNγ | XMG1.2 | BV421 | BioLegend |
| IgD | 11-26c 2a | FITC | BioLegend |
| IgG1, κ | RTK2071 | BV421 | BioLegend |
| IgG2a | R19-15 | Biotin | BD Biosciences |
| IgM | RMM-1 | APC | BioLegend |
| KLRG1 | 2F1 | APC-Cy 7 | BioLegend |
| NK1.1 | PK136 | PE | BioLegend |
| NKp46 | 29A1.4 | PECy-7 | BioLegend |
| TCRβ | H57-597 | PerCP/Cy5.5 | BioLegend |
| TCRγδ | GL3 | BV421 | BioLegend |

Quantification of CMV

Viral DNA Extraction and qPCR

Viremia from plasma was determined by qRT-PCR for the viral gB gene. Briefly, blood was collected from mice by retro-orbital bleed into a MiniCollect K$_2$.EDTA collection tube (Greiner Bio-one, Austria). DNA was extracted using the Qiagen DNeasy Blood and tissue kit (Qiagen, VIC, Australia) as recommended by manufacturer. qRT-PCR was performed from 4 μL DNA with Sso Advanced Universal SYBR green mix (Biorad) and forward (5' ttggctgtcgtctagctgttt 3') and reverse (5' taaggcgtggactagcgataa 3') primers. Serial dilutions of a synthesized MCMV gB sequence (ttggctgtcgtctagctgttttaacgcgcggagtatcaatagagcatcttgctcggtgtaggtcctctccaagccc tttttatcgctgtccacgcctta) were used for the standard curve (range $10^6$-40 genome copies/μL reaction mix). 40 copies/μL reaction mix is the limit of detection established for the assay.

Plaque Forming Units Assay

The mice were sacrificed and organs were collected and snap-frozen in dry ice and stored at −80° C. for later use. To perform plaque assays, organs were thawed and processed as described (Lawson et al., (1988), *Journal of General Virology,* 69: 1987-1998). Briefly, tissues were thawed and homogenized in cold MEM 2% Neonatal Calf serum (NCS, Gibco), and centrifuged to remove insoluble debris. The resulting homogenates were serially diluted and absorbed onto a monolayer of M210B4 cells for 1 h at 37° C. The supernatant was removed and MEM 2% NCS containing 0.01% carboxy-methylcellulose (CMC; Sigma-Aldrich) was overlayed onto the cell monolayer and cells incubated at 37° C., 5% $CO_2$ for 4 days. A solution of 0.5% methylene blue in 10% formaldehyde was added to the cells for 1 day to fix and stain the monolayer. The number of plaques per well were counted using a dissecting microscope and plaque forming units (PFU) per organ calculated.

Complement-Dependent Neutralization Assay

A neutralization assay, based on plaque reduction, was performed as described by Lawson et al. (supra). In brief, serum samples were heated at 56° C. for 30 minutes to inactivate serum complement. Serial dilutions of serum were diluted in MEM in the presence of 5% rabbit serum, as a source of complement, and incubated with 100 PFU K181 MCMV for 1 hour at 37° C. in 5% $CO_2$. Following incubation, the virus-antibody mixture was added to a monolayer of M210B4 cells and incubated for a further 60 minutes at 37° C. in 5% $CO_2$. After incubation, the virus-antibody mixture was removed and the cells overlaid with MEM 2% NCS containing 0.01% carboxy-methylcellulose (CMC; Sigma-Aldrich); the trays were then incubated at 37° C., 5% $CO_2$ for 4 days, then fixed and stained with 0.5% methylene blue in 10% formaldehyde for 1 day prior to plaques being counted. Neutralization titres were recorded as the dilution of serum that gave a 50% reduction in plaque numbers relative to controls incubated in the absence of serum. Four replicates were performed for each dilution of the serum.

CMV Enzyme-Linked Immunosorbent Assay (ELISA)

Enzyme-linked immunosorbent assay (ELISA) was performed as previously described (Lawson et al., supra). MCMV antigen was diluted to the optimum concentration with carbonate/bicarbonate buffer pH 9.5 and incubated at 4° C. for 24 h in 96-well plates. Plates were washed three times with MOBS containing 0.05% Tween 20 and 0.1% bovine serum albumin (Amersham Biosciences). Serum was diluted 1/20 in MOBS containing 0.05% Tween 20 and 1% BSA followed by 12×2-fold serial dilutions. Naïve mouse serum (NMS) was used as a negative control. Sera was added to the plates and incubated for 2 hours at RT in the dark. The plate was then washed 3 times with MOBS containing 0.05% Tween 1% BSA. Anti-MCMV antibodies were detected by adding anti-mouse IgG or IgM-peroxidase conjugate diluted in MOBS containing 0.05% Tween 20 1% BSA. Plates were washed 6 times prior to adding Tetramethylbenzidine substrate (Elisa Systems, QLD, Australia) and left in the dark for 5-20 minutes at RT and terminated by the addition of 1 M sulphuric acid. The absorbance was read at 450 nm using a spectrophotometer (Beckman-Coulter AD-200). The A450 value for each dilution of serum was plotted (y axis) against the $\log_2$ of its dilution factor (x axis). A straight line was fitted to the plot using Prism 6 software, and the serum titre defined as the last dilution preceding the intercept on the x axis.

Spread Inhibition Assay

Spread inhibition was measured using a method based on that described by Cui et al. (2013, *Journal of Virological Methods*, 192: 44-50). Briefly, M210B4 cell monolayers in black-wall clear-bottom 96-well plates were infected with 25 PFU of MCMV-K181Perth-GFP (Wikstrom et al. (2015), *Blood*, 126: 1503-1514). After 6 hours the inoculum was replaced with 200 μl of culture medium containing twofold serial dilutions of serum, and cultured for 5 days. Relative fluorescent units (RFU) were measured using a CLARIOstar plate reader (BMG-Labtech), and monolayers were imaged using an epifluorescence Olympus IX70 microscope with a 2× lens and an Olympus DP70 camera (Olympus). The 50% inhibitory concentration ($IC_{50}$) values were determined by fitting four-parameter curves to plots of the RFU versus $Log_2$ serum dilution using InStat Prism software.

Statistical Analysis

Survival curves were plotted using Kaplan-Meier estimates and compared by log-rank analysis. The curves for leukaemia death were analysed using cumulative incidence analysis of competing risks by R_2.10.1 software. Viremia and PFU data are presented as geometric mean±geometric standard error of the mean (SEM) and other data are represented by mean±SEM. An unpaired 2-tailed Mann-Whitney U test was used to evaluate differences unless stated otherwise *p<0.05, p<0.01, *p<0.001.

Example 1: CMV Reactivation is Dependent on GVHD

In a newly established model of latent MCMV infection, the present inventors investigated the role of BMT and GVHD on MCMV reactivation. Latently infected B6 (H-$2^b$) recipient mice (FIG. 1A) received total body irradiation and were transplanted with uninfected BALB/c (H-$2^d$, MHC-disparate) BM and T cells, or T cell depleted (TCD) BM alone, to generate GVHD and non-GVHD conditions, respectively. In this transplant system, the median survival of mice transplanted with T cell replete grafts was 42 days, and no deaths were observed in mice that received TCD BM alone (FIG. 1B). As expected mice that received BM and T cells developed signs of GVHD (decreased activity, hunching, ruffled fur, and weight loss) with moderate—severe clinical GVHD (score >4) from week 3 post-transplant and clinical scores were <2 in the TCD BM group (FIG. 1C). MCMV reactivation occurred in mice in the GVHD group at 3 weeks post-transplant (FIG. 1D). Viral burden further increased at week 4 in the GVHD group, and was significantly higher than in the non-GVHD group (FIG. 1D). Reactivation occurred in 63% versus 17% of mice in the GVHD and non-GVHD groups, respectively (p<0.05, Chi-square with Yates' correction) (FIG. 1E). MCMV viral load was significantly higher in the liver and lung in the GVHD group, with very few animals in the non-GVHD group having detectable virus (FIG. 1F). MCMV was detected in the salivary gland in the non-GVHD group, but at lower titres than the GVHD group.

Figure 2:
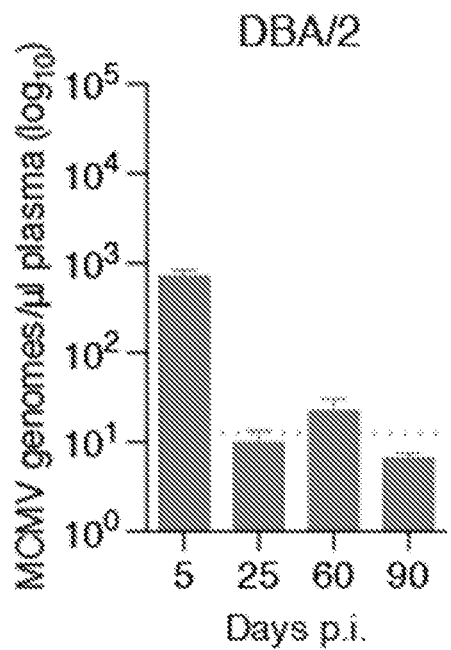
FIG. 2 is a graphical representation showing that CMV reactivation occurs in multiple organs. (A) MCMV viremia in the plasma of DBA/2 mice measured by qPCR after primary MCMV infection. (B-C) DBA/2 mice with a latent MCMV infection were lethally irradiated and transplanted with T cell depleted BM (non-GVHD) or BM+ T cells (GVHD) from naïve BALB/c mice and (B) viremia in the plasma, and (C) viral load in target organs was measured at week 6 post-transplant. Combined data from 2 independent experiments (non-GVHD group, n=8; GVHD group, n=11). (D) Viremia in B6D2F1 mice at the indicated time points after primary infection measured by qPCR is shown (n=6). (E-I) Latently infected B6D2F1 ($H-2^{b/d}$) mice were lethally irradiated and transplanted with TCD BM (non-GVHD) or BM+ T cells (GVHD) from naïve B6 ($H-2^b$) mice. At week 4 post-transplant (E) viremia and (F) viral titres in the indicated organs were quantified (viremia: non-GVHD group, n=10; GVHD group, n=9; viral titres: non-GVHD group, n=9; GVHD group, n=10). Data are combined from 2 experiments. Time course of viral reactivation in B6D2F1 mice was assessed by (G) viremia in the plasma, or (H) viral load within organs (n=7 per time point, combined from 2 experiments). Data is presented as mean±SEM. Statistical significance was assessed with an unpaired two-tailed Mann-Whitney. *$p<0.05$, $p<0.01$, *$p<0.001$. (I) Tissue sections from B6D2F1 mice with GVDH. MCMV-infected cells in various organs were identified by X-gal staining. Bar=200 μm except for gut sections where bar=300 μm. Dotted line represents limit of detection.
Figure 2:
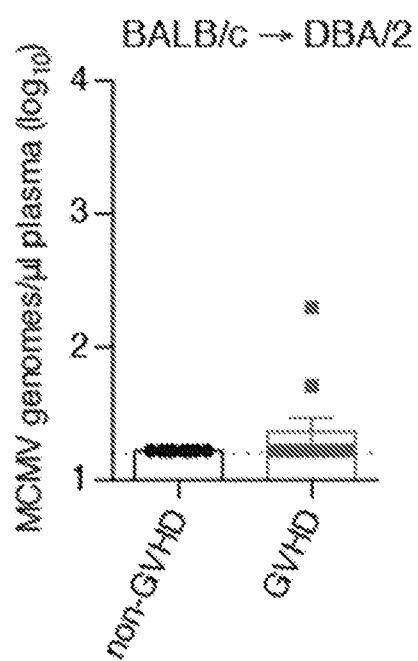
Figure 2:
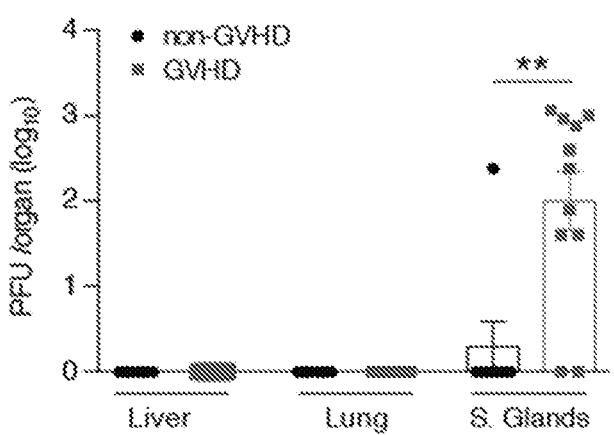
Figure 2:
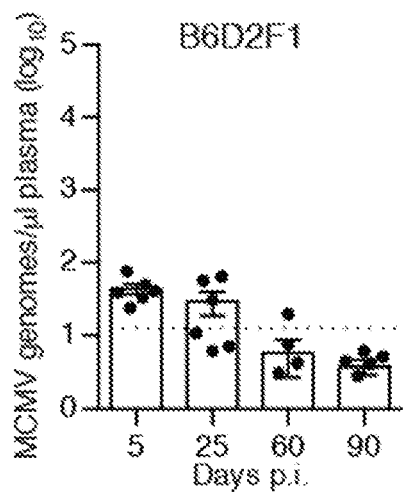
Figure 2:
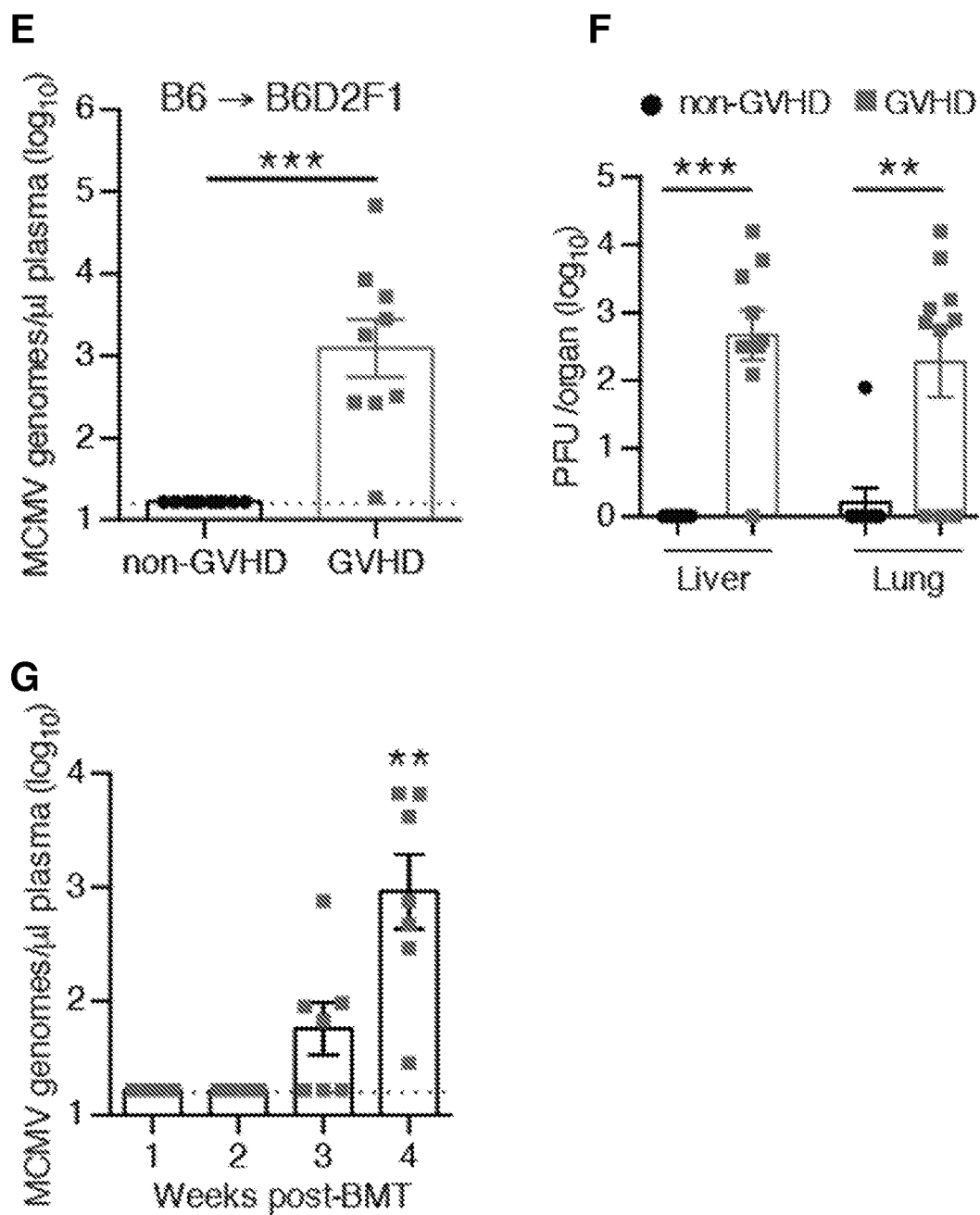
Figure 2:
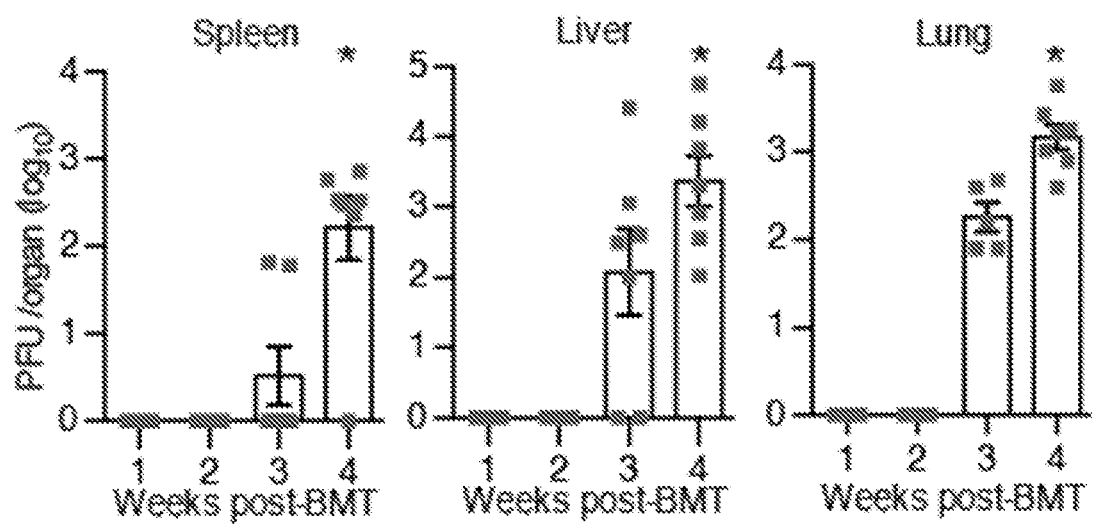
Figure 2:
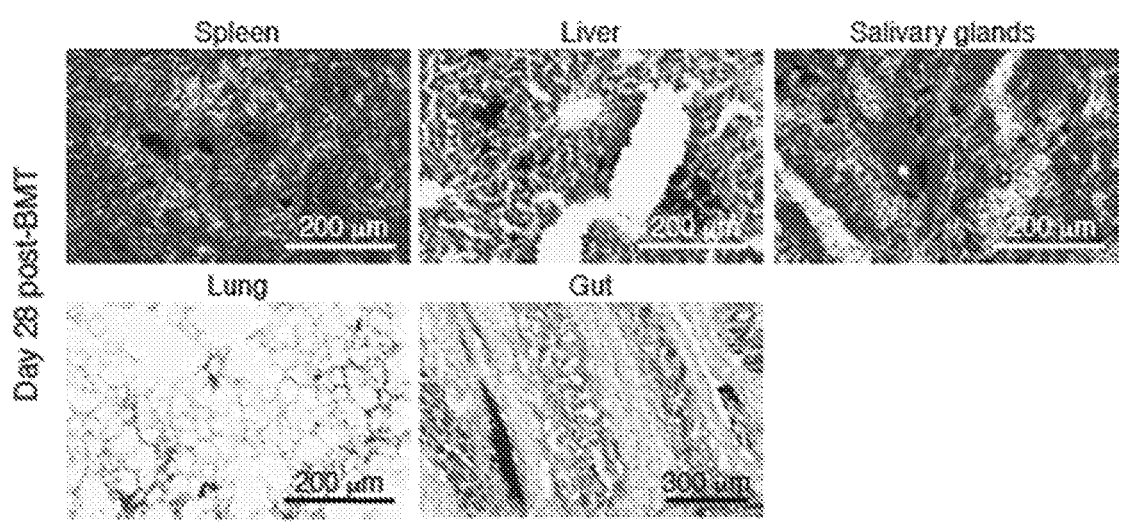

These findings are broadly consistent across different transplant models. In the B6→BALB/c MHC-disparate model, significant viremia was observed at week 5 post-transplant in the GVHD group but not the non-GVHD group (FIG. 1H). In this system, both the frequency and level of viremia were low. As is the case with the BALB/c→B6 model, MCMV replication was detected in the salivary gland in both non-GVHD and GVHD groups but in lungs and liver only in the GVHD group (FIG. 1I). MCMV reactivation occurred much less readily in an MHC-matched (minor histocompatibility antigen mismatched) BALB/c (H-$2^b$)→DBA/2 (H-$2^b$) system (FIG. 2A), with only 2 out of 11 mice in the GVHD group having detectable viremia (FIG. 2B) and no virus detectable in the liver and lungs in either group (FIG. 2C). In the salivary glands, the frequency of reactivation and viral titres were significantly higher in the GVHD group (FIG. 2C). In a further system, B6D2F1 mice underwent a primary infection and viremia was quantified (FIG. 2D). These B6D2F1 recipients (H-$2^{b/d}$) (FIG. 2D) underwent haploidentical transplant with B6 (H-$2^b$) donors, where a shared MHC allele allows for cognate T cells interaction with APCs. Significant viremia was observed in the GVHD group at 4 weeks post-transplant (FIG. 2E) and virus was detected in the liver and lung (FIG. 2F). There was no significant virus reactivation in the non-GVHD group.

Example 2: CMV Reactivation Occurs in Multiple Organs

The pathogenesis of acute CMV infection is greatly influenced by its broad range of target cells and reactivation is commonly associated with multi-organ disease (Schmidt et al., (1991) *The New England Journal of Medicine*, 324). In order to investigate the cell types involved in CMV reactivation and subsequent amplification by lytic replication, B6D2F1 mice were latently infected with MCMV-K181Perth-LacZ. This virus co-expresses the LacZ reporter gene with McK2 (m131-129), but replicates as MCMV-K181Perth. Latently infected B6D2F1 mice were lethally irradiated and transplanted with BM and T cells from haploidentical donor B6 mice. Viremia and viral replication in the organs were determined weekly and lungs, liver, spleen, salivary glands and gut were collected and stained for β-galactosidase (LacZ) activity. Positive stain is indicative of actively replicating virus.

MCMV reactivation was not detected in B6D2F1 recipients for the first 2 weeks post-transplant in plasma (FIG. 2G) or target organs (FIG. 2H) but became detectable after 3 weeks with the appearance of plasma viremia and viral replication by X-gal staining in organs (FIG. 2I). The number of viral foci was highest in the liver and lungs at this early time-point, but foci, albeit in lower numbers, were also observed in the gut and spleen (FIG. 2I). At 4 weeks post-transplant, significant reactivation had occurred with increased viremia (FIGS. 2E and G), viral titres (FIGS. 2F and H), and larger and more frequent viral foci detected by X-gal staining (FIG. 2I).

Figure 3:
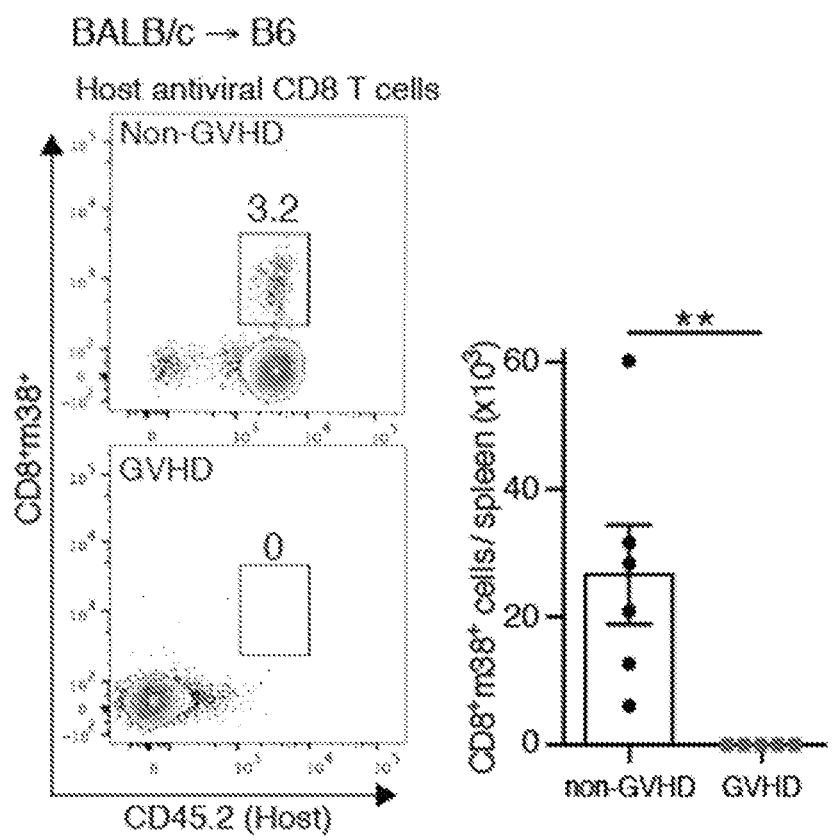
FIG. 3 is a graphical representation showing that loss of T cells and/or natural killer (NK) cells is insufficient to induce MCMV reactivation. Latently infected B6.CD45.2 mice were transplanted with BALB/c.CD45.1 TCD BM (non-GVHD) or BM+ T cells (GVHD). At day 14 post-transplant the frequency and number of anti-viral CD8+ T cells were assessed by FACS analysis. Representative FACS plots and total number of (A) host-derived $K^b$ restricted m38+ CD8+ T cells, or (B) donor-derived $L^d$ restricted IE1+ CD8+ T cells are shown (non-GVHD, n=6; GVHD, n=5). The data are representative of 2 experiments. (C-D) DBA/2 mice with a latent MCMV infection were lethally irradiated and transplanted with TCD BM (non-GVHD) or BM+T cells (GVHD) derived from naïve BALB/c mice. (C) At day 14 post-transplant host-derived IE1+ CD8+ T cell frequency and total cell number were assessed. (D) Splenocytes isolated from non-GVHD mice 14 days post-transplant were stimulated in-vitro with IE1-peptide for 4 hours and stained for IFNγ. Representative FACS plots and frequency of IE1-specific CD8+ IFNγ producing cells are shown. Data from 1 experiment (n=3 per group). (E) Latently infected B6D2F1 were transplanted with TCD BM (non-GVHD) or BM+T cells (GVHD) from B6 mice and 14 days post-transplant the number of donor virus-specific m38+ and host IE1+ CD8+ T cells in the spleen quantified (non-GVHD, n=7; GVHD, n=7). Data are combined from 2 experiments. (F) Latently infected B6D2F1 mice were transplanted with TCD BM from B6.WT or B6.TCRδ$^{-/-}$ mice as indicated. Depleting antibodies were administered to eliminate host and reconstituting donor CD4+ T cells, CD8+ T cells and NK cells. Viremia in blood at 4 weeks (GVHD) and 6 weeks (non-GVHD) post-transplant is shown. (GVHD group, n=8; non-GVHD groups, n=7). Data are combined from 2 experiments. Data represent mean±SEM. *$p<0.05$, $p<0.01$, *$p<0.001$ (Mann-Whitney U test). Dotted line represents limit of detection.
Figure 3:
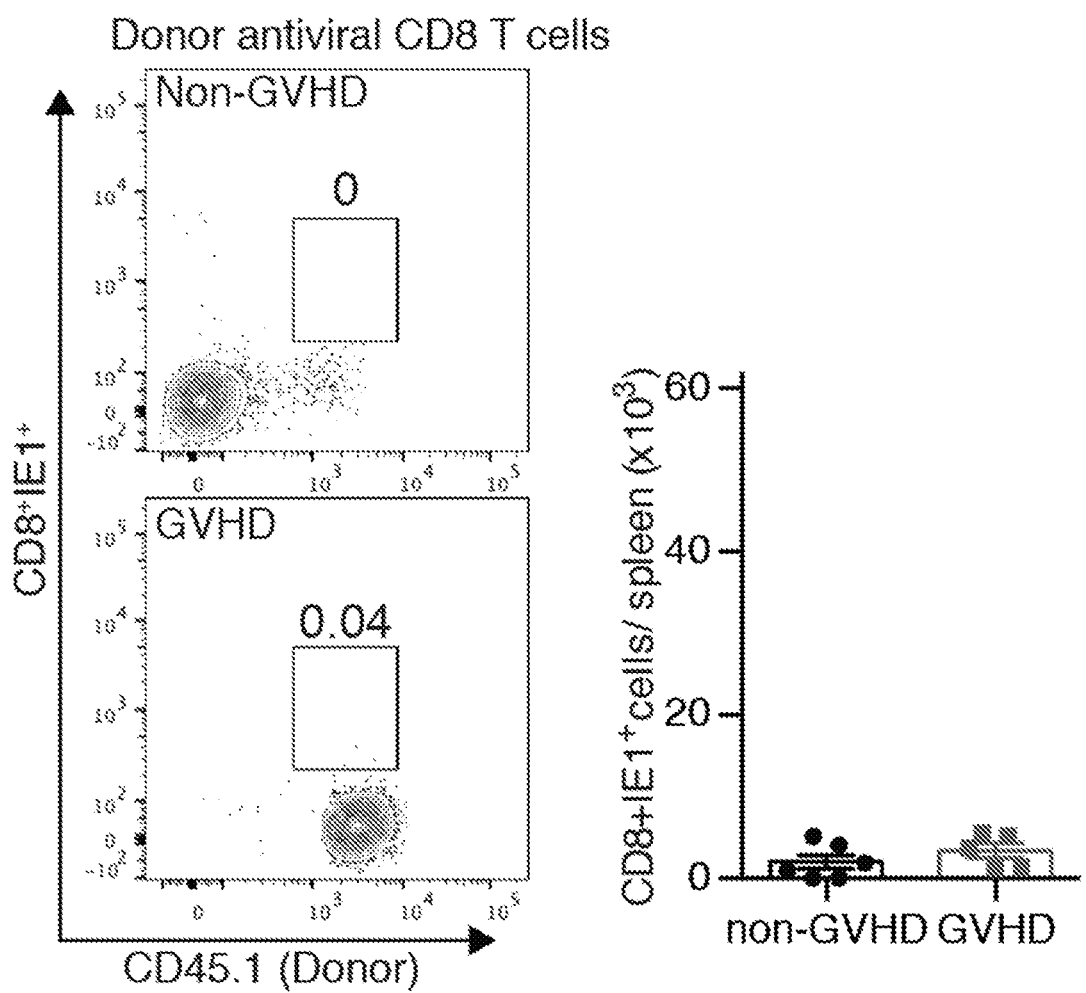
Figure 3:
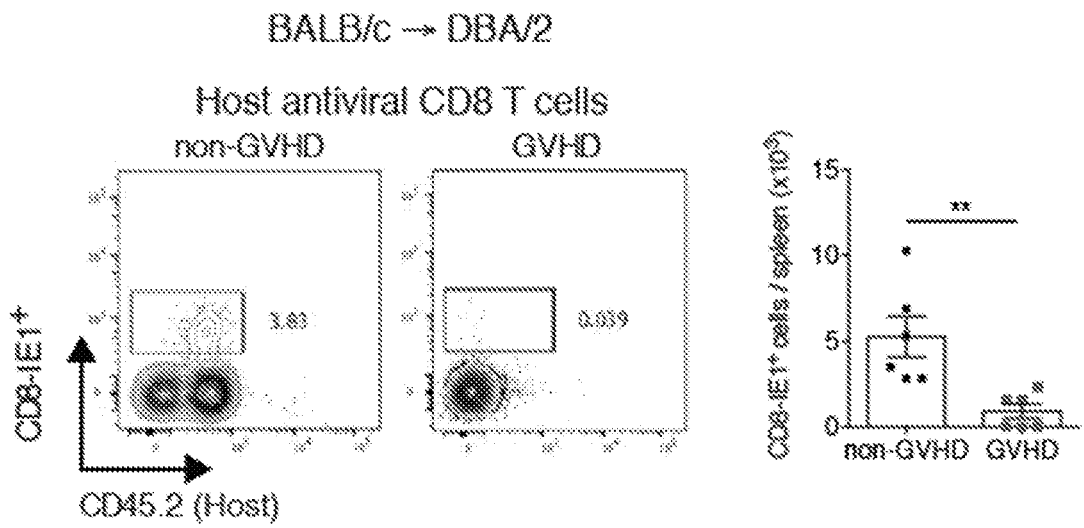
Figure 3:
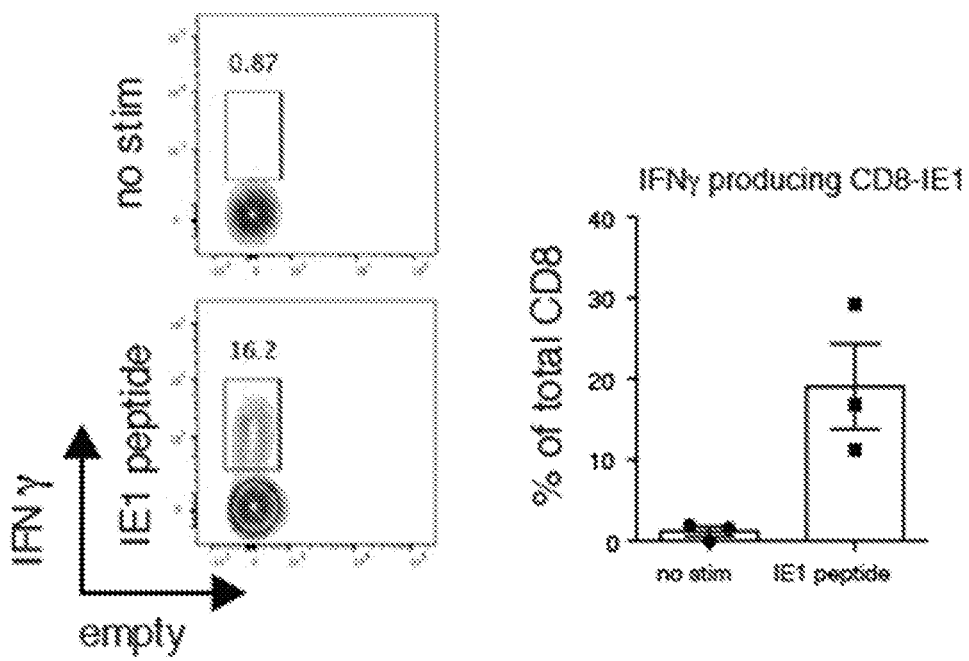
Figure 3:
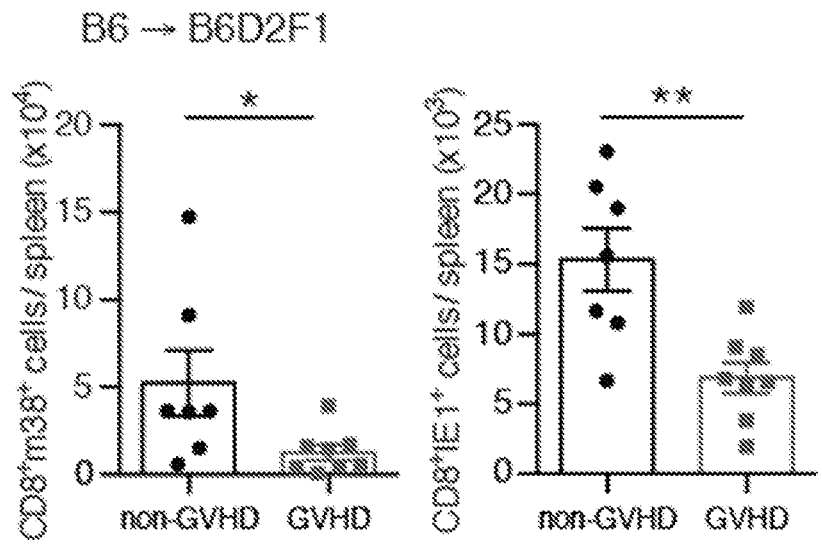
Figure 3:
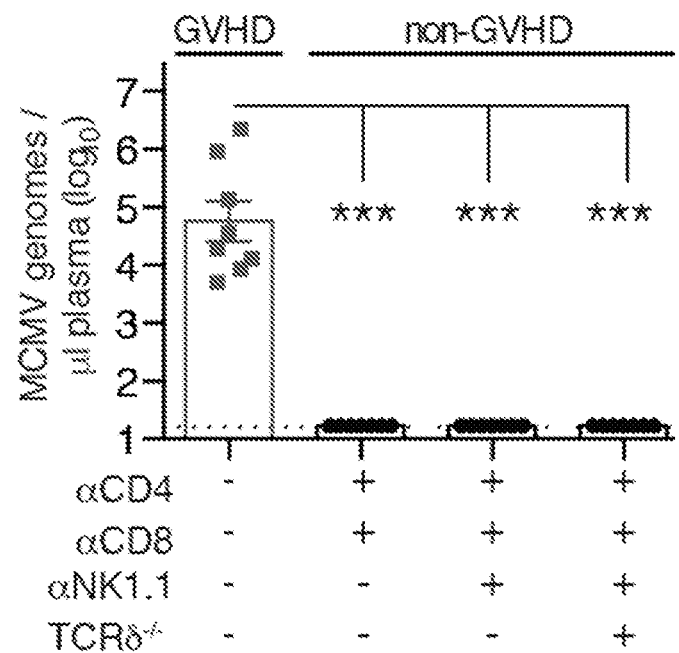

Example 3: T and NK Cell Lymphopenia Alone are Insufficient to Induce MCMV Reactivation To investigate the underlying mechanism of MCMV reactivation in GVHD, and protection in non-GVHD mice, latently infected B6 (H-$2^b$) recipient mice were transplanted with TCD BM alone or BM+T cells from BALB/c (H-$2^d$, CD45.1$^+$) donors. At day 14 post-transplant host m38-specific antiviral T cells were quantified using tetramers. Host m38-specific T cells were detected in the non-GVHD group, while these cells were absent in GVHD mice (FIG. 3A). Anti-viral T cells of donor origin were not detected in non-GVHD or GVHD mice (FIG. 3B). DBA/2 (H-$2^d$, CD45.2$^+$) latently infected mice were also transplanted with TCD BM or BM+T cells from MHC matched BALB/c (H-$2^d$, CD45.1$^+$) donors. At day 14 post-transplant, >99% of splenic CD8 T cells in the GVHD group were of donor origin, as a result of the donor alloreactive response to minor recipient antigens. As expected, in non-GVHD conditions, there was partial donor T cell chimerism, with 29±7% donor T cells. Antiviral CD8$^+$ T responses were measured using IE1-specific tetramers. CMV-specific CD8$^+$ T cell responses were low in the GVHD group (0.9±0.4×$10^3$ cells per spleen). Significantly more recipient (CD45.2$^+$) IE1-specific cells were present in the non-GVHD group (5.3±1.2×$10^3$ cells per spleen) (FIG. 3C) and these cells produced IFNγ upon stimulation with IE1 peptides (FIG. 3D). These data corroborate findings from others that demonstrated the lack of CMV-specific CD8$^+$ T cell responses in the presence of GVHD (Wikstrom et al., (2015), *Blood*, 126: 1503-1514). Furthermore, the present inventors have shown that, in the absence of donor T cell-mediated alloreactivity, recipient MCMV-specific T cells persist (FIG. 3E) and remain functional, and therefore can potentially provide adequate T cell mediated protection from reactivation.

To test this hypothesis further, the present inventors performed BMT in a B6→B6D2F1 system with sustained CD4$^+$, CD8$^+$ and NK1.1$^+$ immunodepletion. An additional group received TCRδ KO grafts together with immunodepletion to exclude any protective effect from γδ T cells. MCMV viremia was quantified 3 weeks post-transplant and weekly thereafter. Interestingly, MCMV was undetectable in the plasma of all mice for at least 6 weeks post-transplant (FIG. 3F) despite effective T and NK cell depletion. These results suggest that T, NK and γδ T cells, recipient and/or donor-derived, are not essential for protection from MCMV reactivation in the absence of GVHD.

Figure 4:
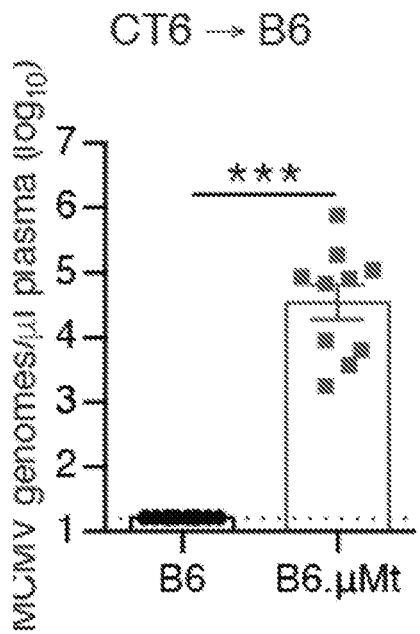
FIG. 4 is a graphical representation showing that humoral immunity protects from MCMV reactivation in the absence of T cells and/or NK cells. Latently infected WT B6 or B6.μMT mice were lethally irradiated and transplanted with TCD BM from naïve CT6 mice (BALB/c NK1.1+). CD4, CD8 and NK1.1 depleting antibodies were administered to both groups of mice post-transplant. (A) Viremia at 14 days post-transplant and (B) viral titres in target organs at day 16 post-transplant are shown. (B6.WT, n=10; B6.μMt, n=8-9). Data are combined from 2 experiments. (C) A complement-dependent neutralization assay was used to measure MCMV-specific antibody titre pre-transplant. (D) MCMV-specific IgM (left panel) and total IgG (right panel) antibodies were determined by ELISA at day 16 post-transplant (B6.WT n=5; B6.μMt n=3). (E-F) Latently infected B6 or B6.μMT mice were transplanted with CT6 BM or BM+T cells with one group of B6.μMT mice also treated with CD4, CD8 and NK1.1 depleting antibodies post-transplant as indicated. (E) Viremia was measured by qPCR at the indicated time points p.i. (F) Viral titres in the organs at the time of death were measured by plaque assay. (n=4-5 per time point). Data in (E-F) are representative of 2 experiments. *$p<0.05$, $p<0.01$, *$p<0.001$ (Mann-Whitney U test). Dotted line represents limits of detection.
Figure 4:
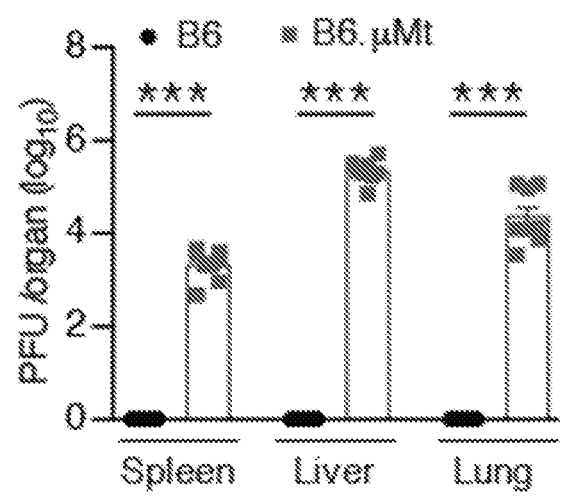
Figure 4:
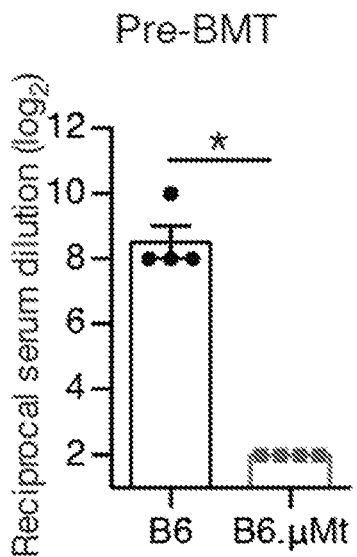
Figure 4:
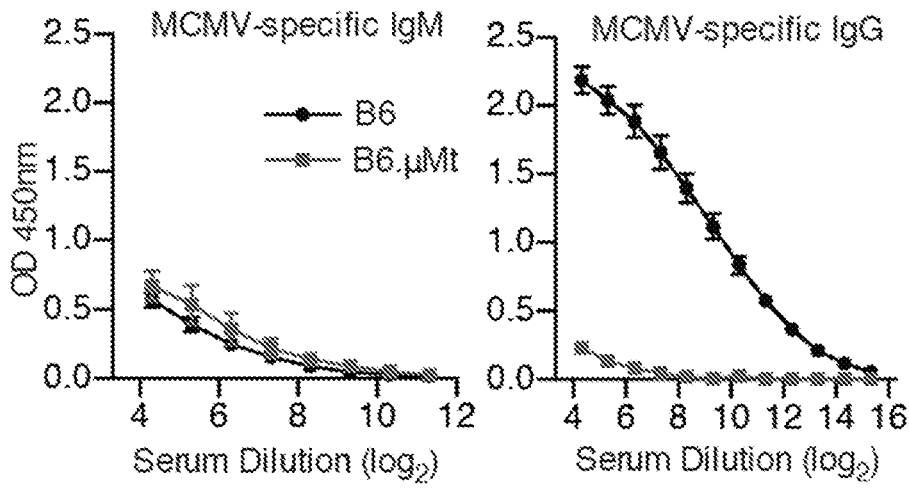
Figure 4:
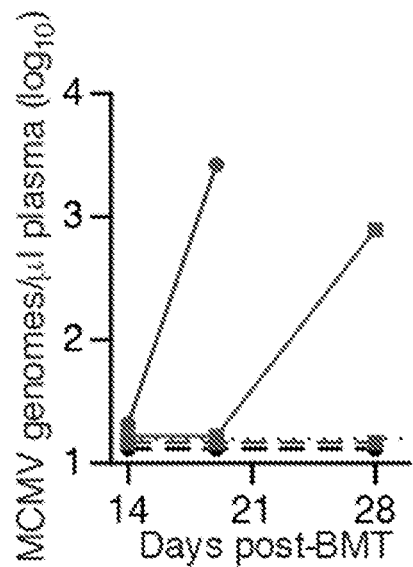
Figure 4:
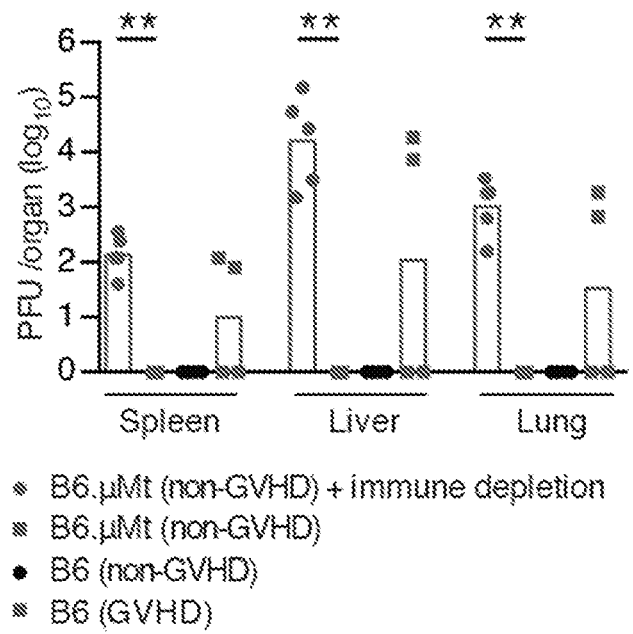

Example 4: Humoral Immunity Protects from MCMV Reactivation in the Absence of T and NK Cells The lack of MCMV reactivation observed in non-GVHD mice despite sustained T-cell and NK cell depletion suggests that humoral immunity may be sufficient to protect from viral reactivation in the absence of GVHD. To determine the role of antibodies, the present inventors used µMt KO mice, which lack mature B cells and therefore cannot produce antibodies. These mice were latently infected and transplanted with CT6 (NK1.1$^+$ BALB/c) TCD BM alone followed by continuous treatment with αCD4$^+$, αCD8$^+$ and αNK1.1$^+$ depleting antibodies to eliminate CD4 and CD8 T cells and NK cells. By day 14, mice exhibited severe hunching, ruffling and reduced activity, and were sacrificed at day 16. MCMV reactivation was detected in all µMt KO recipients with high-level viremia (FIG. 4A) and substantial viral loads in target organs (FIG. 4B). Post-transplant, µMt mice which lacked MCMV-neutralizing antibodies pre-transplant (FIG. 4C), showed low levels of MCMV-specific IgM equivalent to those in B6 wild-type (WT) recipients, but lacked MCMV-specific IgG antibodies (FIG. 4D).

These data suggest that in the absence of T and NK cells, antibody-mediated immunity is sufficient to protect from MCMV reactivation. To confirm that antibody-mediated immunity is essential and sufficient to prevent MCMV reactivation and determine whether the additional absence of T-cells and NK cells is important, the present inventors transplanted latently infected µMt KO recipients with BM only, with or without post-transplant immunodepletion. MCMV reactivation occurred only in the immunodepleted group but, no reactivation was observed in the non-immunodepleted group either in plasma or target organs (FIGS. 4E and F). These results suggest that whilst humoral immunity is sufficient, it is not required for controlling MCMV reactivation if T and NK cells are present. Thus, humoral immunity is sufficient to curb viral reactivation post-transplantation, but MCMV reactivation requires the combined lack of antibodies, T-cells and NK cells.

Example 5: Deficient Humoral Immunity Contributes to MCMV Reactivation in GVHD

Figure 5:
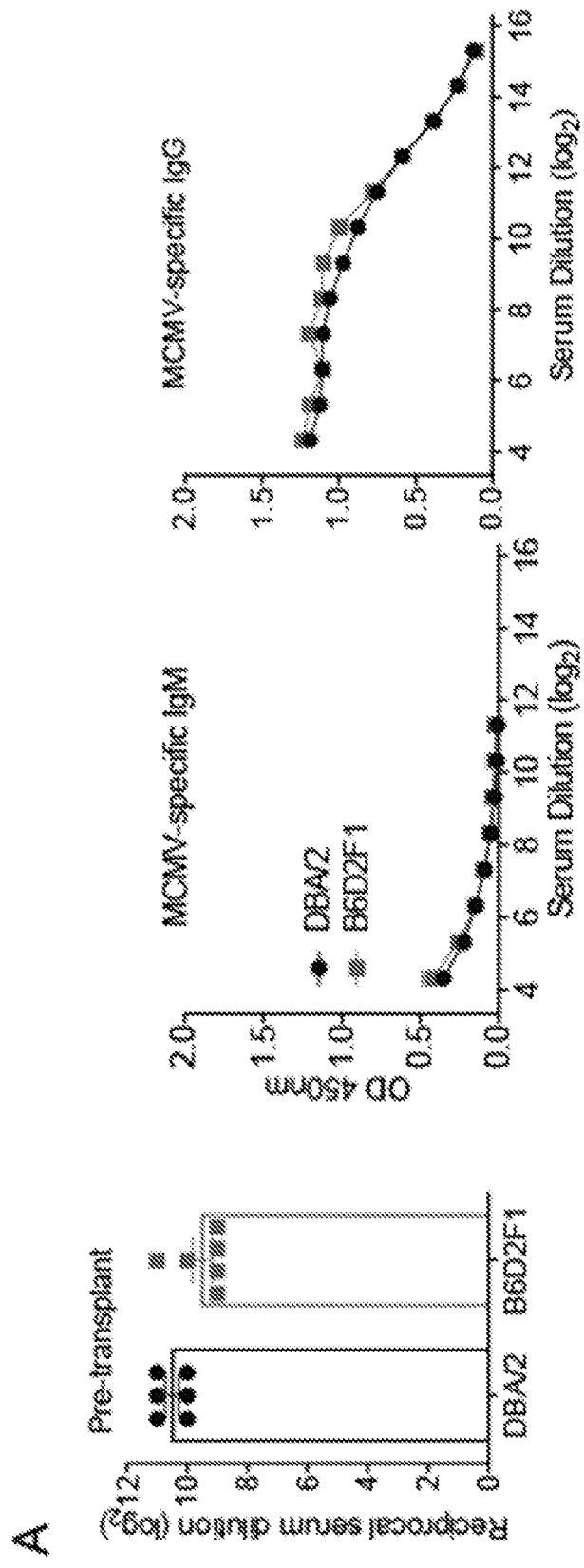
FIG. 5 is a graphical representation showing that deficient humoral immunity contributes to CMV reactivation in GVHD. (A) MCMV-specific neutralizing antibodies and MCMV-specific IgM and IgG antibodies in latently infected DBA/2 and B6D2F1 mice were quantified. (B-C) Latently infected DBA/2 mice were transplanted with BALB/c BM (non-GVHD) or BM+T cells (GVHD). (B) The levels of MCMV neutralizing antibodies at day 7 post-transplant and (C) the levels of MCMV-specific IgM and IgG antibodies at day 28 post-transplant were measured. (D) Latently infected B6D2F1 mice were transplanted with B6 BM with or without T cells and MCMV-specific IgM and IgG antibodies in latently infected B2D2F1 mice post-transplant were measured (n=6 per group). MCMV-specific IgG titres are shown in the far right graph. Data are representative of 2 experiments wherein n=4 mice/group. (E) Latently infected B6D2F1 hosts were transplanted with B6 or B6.FcγR III KO, TCD BM (non-GVHD) or BM+T cells (GVHD). Anti CD4, CD8 and NK1.1 antibodies were administered as indicated. Viremia levels at 4 weeks post-transplant are shown. n>8 per group combined from 2 experiments. (F) Neutralizing antibodies at day 7 and day 28 post-transplant were assessed (non-GVHD n=11; GVHD n=12). Data are combined from 2 experiments. (G) M210B4 stromal cells were infected with a GFP-expressing MCMV. Serial dilutions of NMS (naïve mouse serum), or serum isolated from non-GVHD or GVHD mice at either day 14 or day 28 post-BMT were added to the cultures 6 hours p.i. Representative images of wells 5 days p.i. are shown. The GFP signal was quantified and a 50% inhibitory concentration determined and is shown in Table 6. Data represent mean±SEM. $*p<0.05$, $p<0.01$, $*p<0.001$, $****p<0.0001$ (Mann-Whitney U test). Dotted line represents limit of detection.
Figure 5:
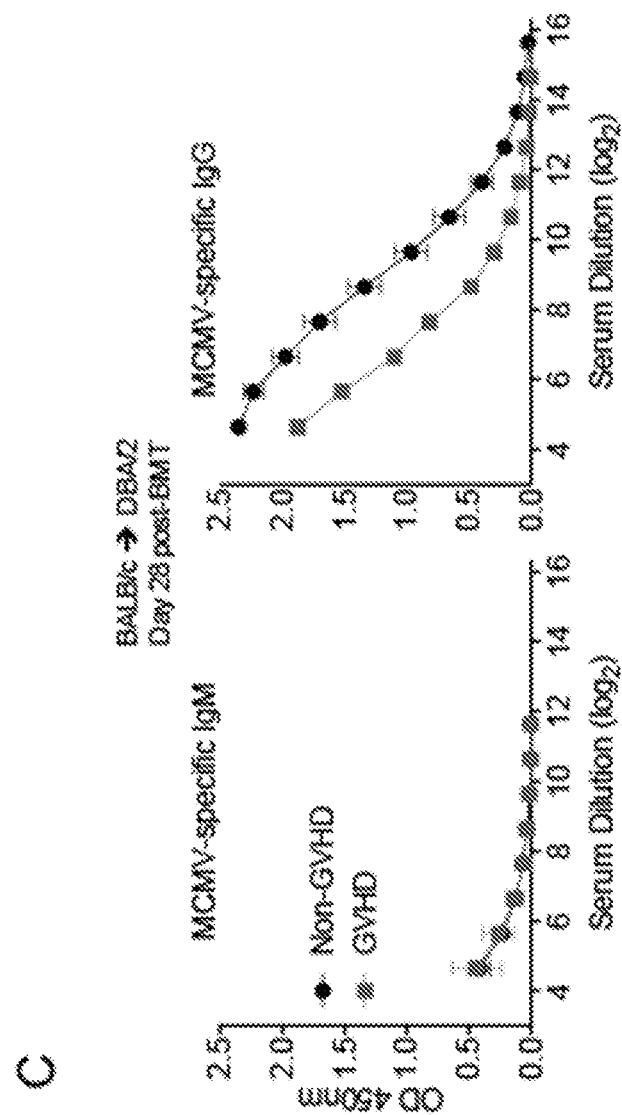
Figure 5:
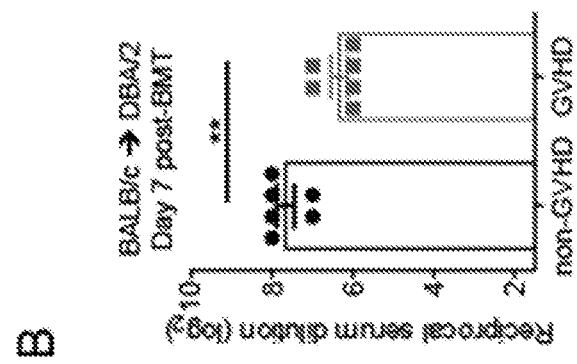
Figure 5:
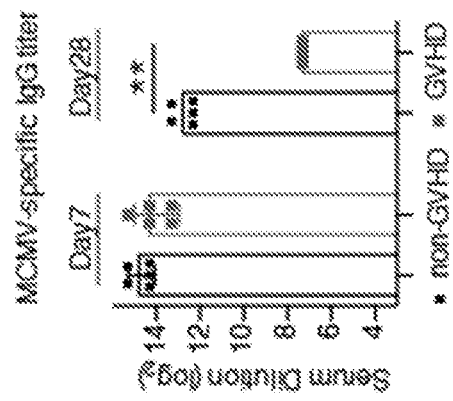
Figure 5:
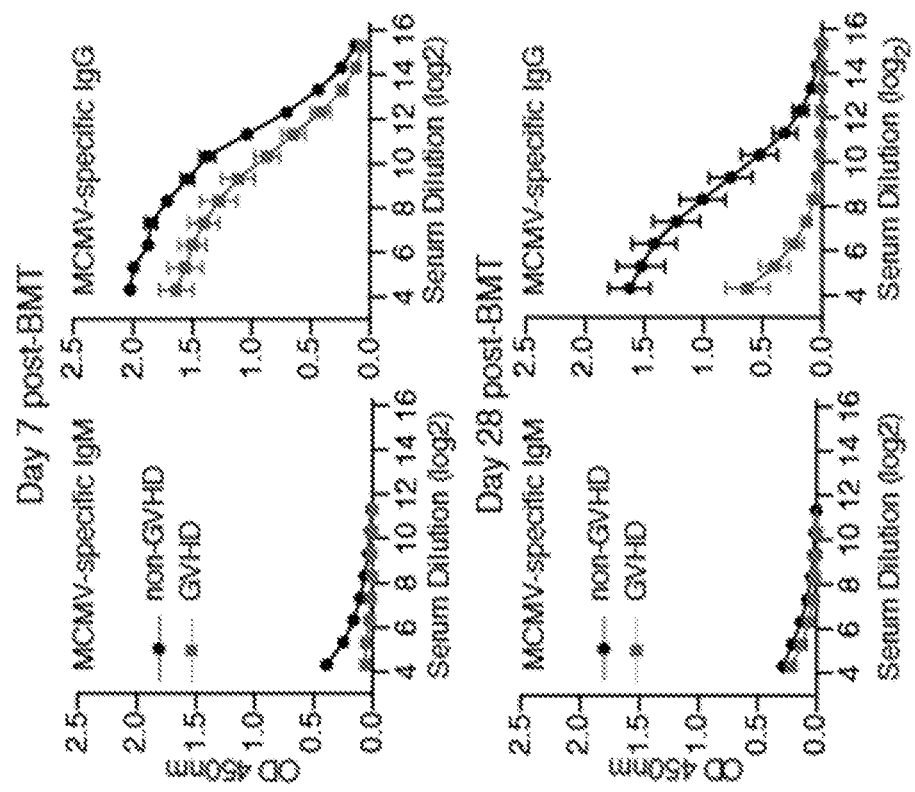
Figure 5:
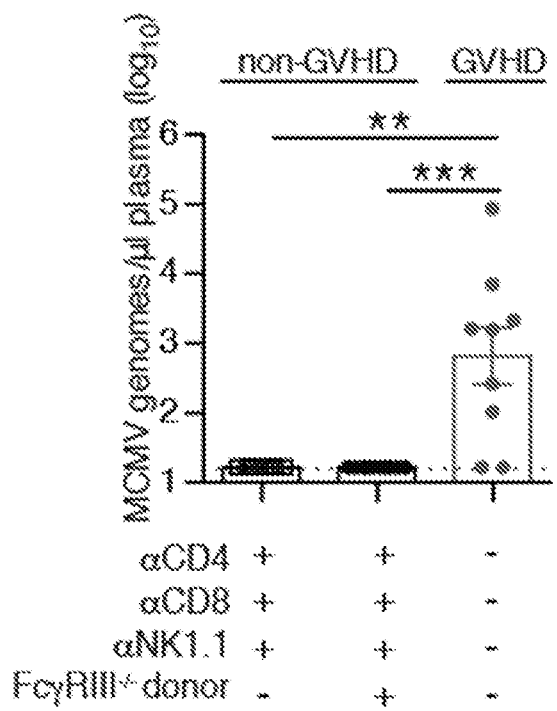
Figure 5:
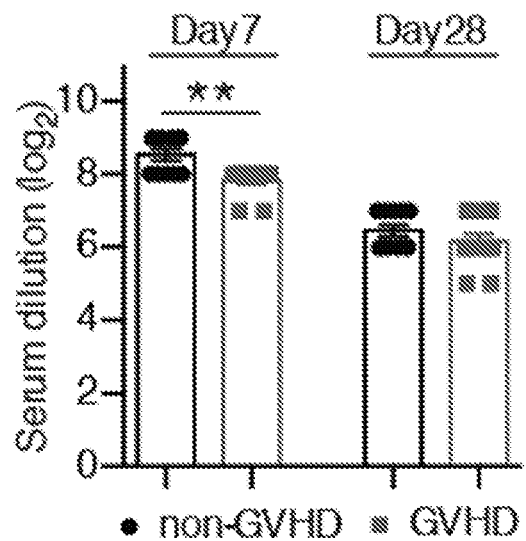
Figure 5:
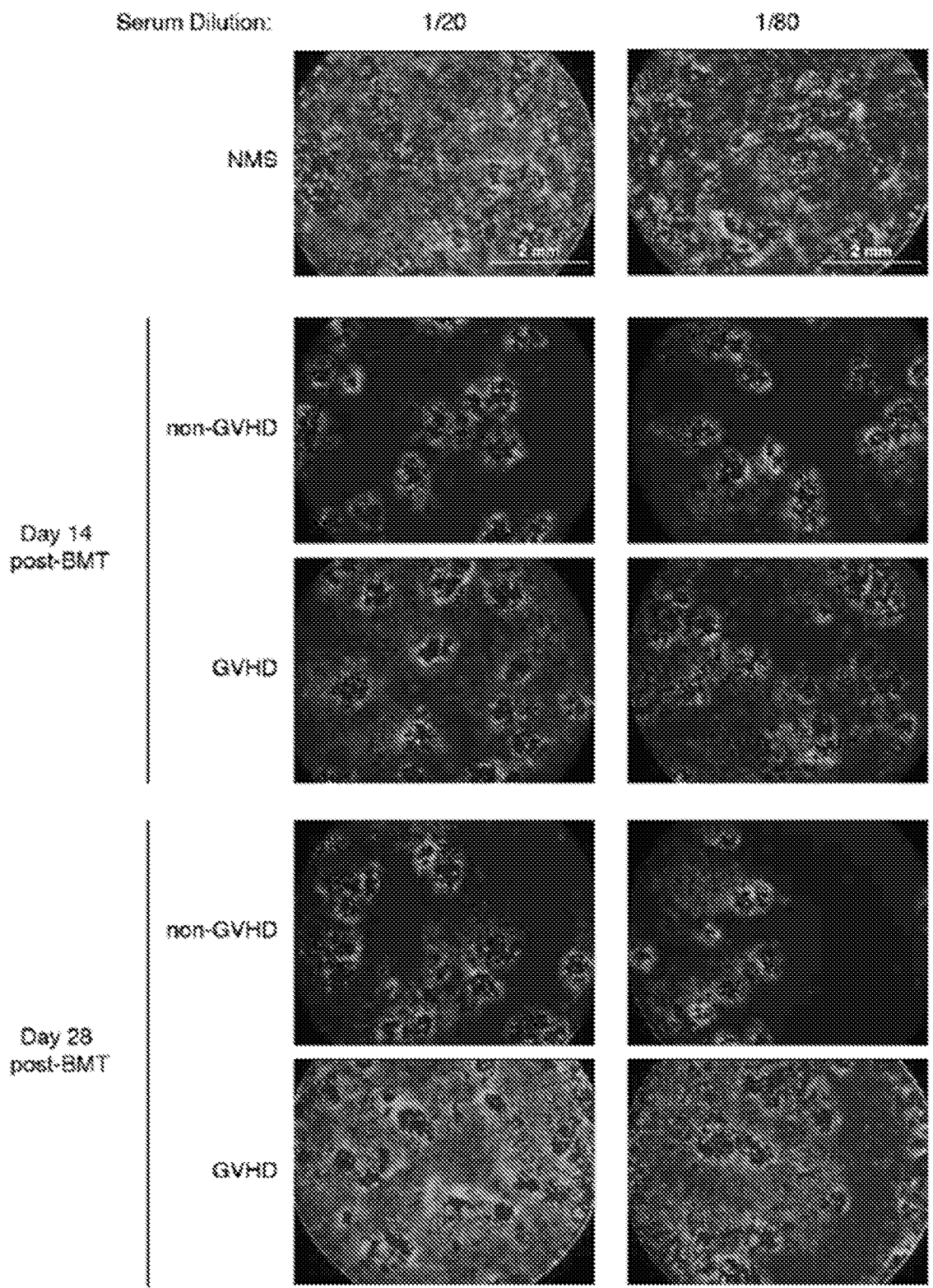

Considering the protective role of the humoral immunity, the present inventors next investigated the role of GVHD on serum antibody levels. Serum from latently infected DBA2 and B62F1 mice neutralized MCMV in vitro, and contained high levels of MCMV-specific IgG pre-transplant (FIG. 5A). In a BALB/c→DBA/2 transplant, at day 7 post-transplant, mice with GVHD had lower levels of MCMV-neutralizing antibodies (FIG. 5B). At 28 days after BMT, mice with GVHD had significantly lower levels of circulating MCMV-IgG antibodies (FIG. 5C). Similar differences in MCMV-specific IgG antibodies were detected in B6→B6D2F1 haploidentical transplants. In transplanted mice with GVHD there was a reduction in the levels of MCMV-specific IgG commencing at day 7 post-transplant, which became significant by day 28 post-transplant (FIG. 5D). MCMV-specific IgM antibodies were scant/absent in both GVHD and non-GVHD hosts (FIG. 5D). Immunoglobulin Fc gamma receptor III (FcγR III) subunit is a component of the low affinity receptor for IgG on macrophages, monocytes, NK cells, eosinophils and dendritic cells (Takai (2002), *Nature Reviews Immunology*, 2: 580-592). FcγR III deficient mice are unable to phagocytose Ab-coated particles and have defective NK cell-mediated Ab-dependent cytotoxicity. Interestingly MCMV reactivation did not occur in BMT with donor FcγR III KO TCD BM and immunodepletion (FIG. 5E). This suggests that the MCMV-neutralizing antibodies have a FcγR III independent effect. Interestingly, there was no detectable MCMV-specific IgM in either GVHD or non-GVHD group but IgG$^{MCMV}$ levels were higher in the non-GVHD group compared to mice in the GVHD group, with an 8 and 32 fold difference in total IgG$^{MCMV}$ titres in the BALB/c→DBA/2 and B6→B6D2F1 systems, respectively (FIGS. 5C and D). These results suggest that MCMV-specific IgG may be sufficient to protect from MCMV reactivation, and this protective pathway is disrupted by GVHD.

The capacity of immune serum to neutralize cell-free virus and inhibit viral spread was also evaluated. The neutralizing capacity of antibodies present in the serum of mice at day 28 post-transplant was not significantly different between GVHD and non-GVHD groups (FIG. 5F). In contrast, serum isolated from mice with GVHD at day 28 post-transplant showed a complete inability to inhibit cell-to-cell spread of MCMV in vitro (Table 6, and FIG. 5G). Thus, inhibition of cell-to-cell spread in vitro is the best indicator of protective capacity in vivo and the results indicate that this is a major mechanism by which antibodies impact on viral reactivation and spread in latently infected hosts after BMT.

TABLE 6

Quantification of Viral Spread Inhibition

| Days post-BMT | Group | IC$_{50}$ Spread Inhibition (Log$_2$)$^a$ |
| --- | --- | --- |
| 14 | Non-GVHD | 6.265 ± 1.349 |
| 14 | GVHD | 6.132 ± 1.754 |
| 28 | Non-GVHD | 6.721 ± 0.386 |
| 28 | GVHD | No inhibition$^b$ |

$^a$Data are expressed as reciprocal Log$_2$ dilution of serum required to inhibit viral spread by 50%.
$^b$No inhibition of viral spread detected at the lowest tested dilution (1/20).

Figure 6:
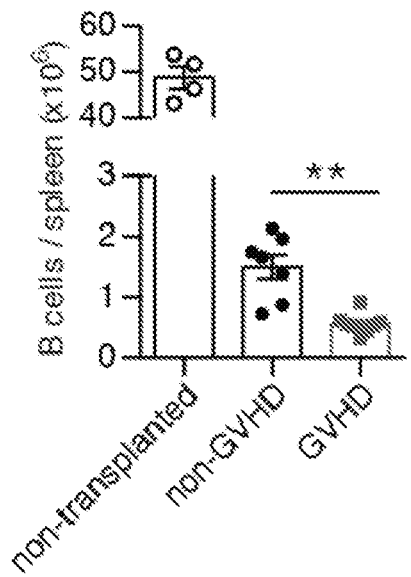
FIG. 6 is a graphical representation showing that the transfer of serum from latently infected mice prevents MCMV reactivation. (A) Number of mature B cells in the spleen and (B) plasma cells in the bone marrow in latently infected B6D2F1 mice 14 days post-transplant (non-GVHD n=7, GVHD n=8), or non-transplanted controls. Data are combined from 2 experiments. (C) The relative contribution of host and donor cells to the plasma cell pool was determined by staining with CD45.1 and CD45.2 antibodies. Data are combined from 2 experiments. (D-F) Latently infected B6D2F1 mice were transplanted with B6 BM and T cells. Serum from latently infected (seropositive) or uninfected (seronegative) BALB/c mice was injected twice weekly post-transplant. (D) GVHD scores in mice receiving serum from seronegative (black) and seropositive (grey) donors. (E) Viremia at 3 and 4 weeks post-transplant. (F) Viral titres in organs at 4 weeks post-transplant (seronegative n=9; seropositive n=10). Data are combined from 2 experiments. (G) Serum collected from non-GVHD and GVHD groups at day 14 and day 28 post-transplant (as per schema), naïve mouse serum (NMS), or serum from latently infected mice (Immune Serum (IMS)) was injected in BALB/c weaners (3 weeks of age) and 24 hr later the mice were infected with MCMV. Viral titres quantified 4 days p.i. are shown. Data are combined from 3 experiments. (H) IMS collected from BALB/c mice latently infected with K181 (K181 IMS), or NMS, was injected into BALB/c weaners prior to infection with K181, N1, G4, or G5 viral isolates. The transferred serum volumes are indicated. Viral titres in the organs were measured 4 days p.i. Data are combined from 2 experiments (n=3-6/group/experiment). (I) Serum collected from BALB/c mice latently infected with the N1 strain (N1 IMS), or NMS, was transferred to BALB/c weaners prior to infection with the K181 or N1 viral strains. Viral titres in the organs were measured 4 days p.i. Data are combined from 2 experiments (n=2-3/group/experiment). (J-K) B6D2F1 mice latently infected with MCMV K181 were transplanted with B6 BM+T cells to induce GVHD. NMS or serum from mice latently infected with K181, N1, or sera pooled from mice individually infected with one of eight different MCMV isolates (including K181) was injected twice weekly from day 14 post-transplant. (J) Viremia and (K) viral titres in organs at 4 weeks post-transplant. Data are combined from 2 experiments (n=3-4/group/experiment). Data represent mean±SEM $*p<0.05$. $p<0.01$, $*p<0.001$ (Mann-Whitney U test used for all analysis except (J, K) where Kruskal-Wallis was used.
Figure 6:
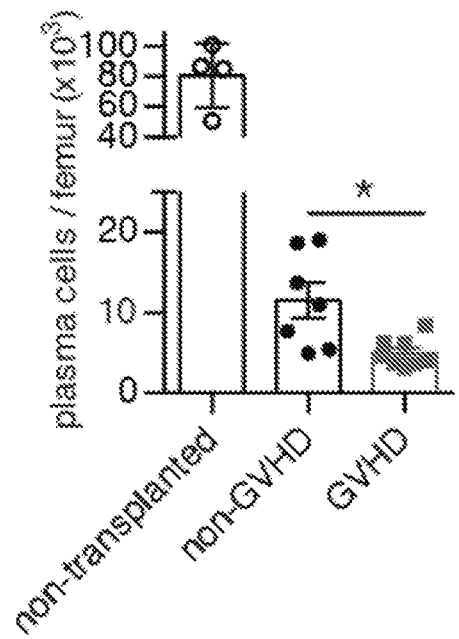
Figure 6:
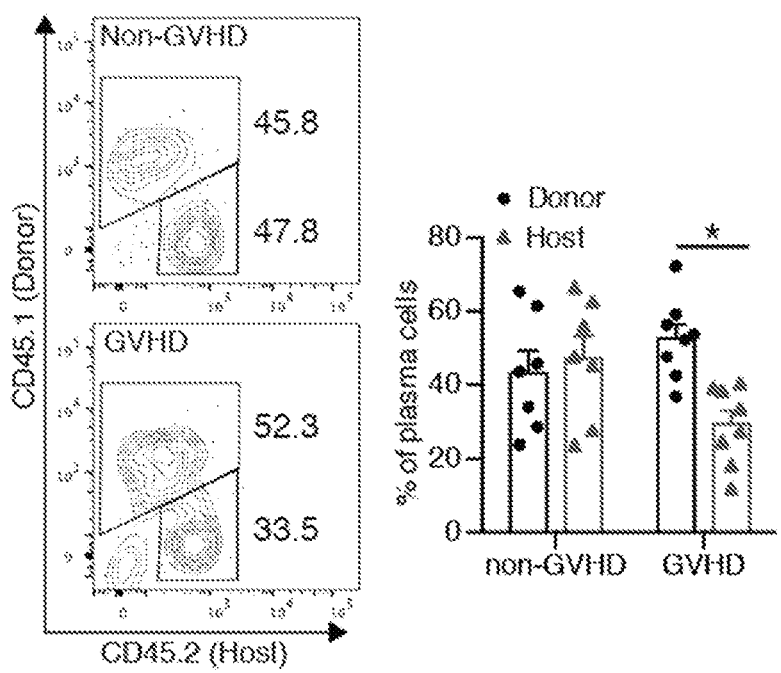
Figure 6:
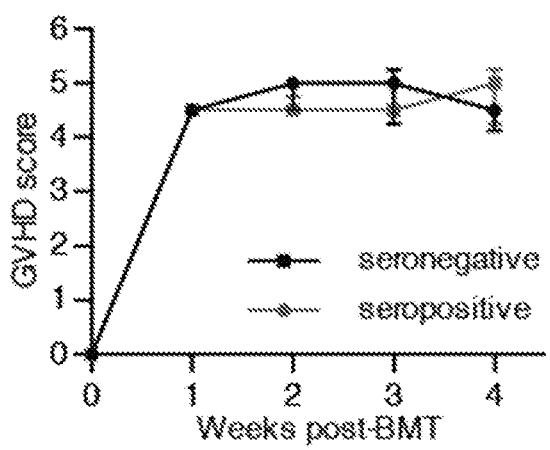
Figure 6:
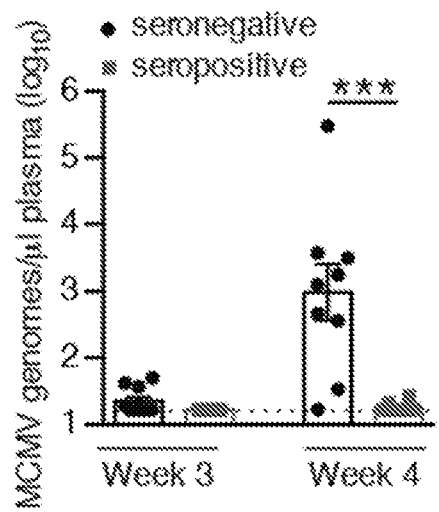
Figure 6:
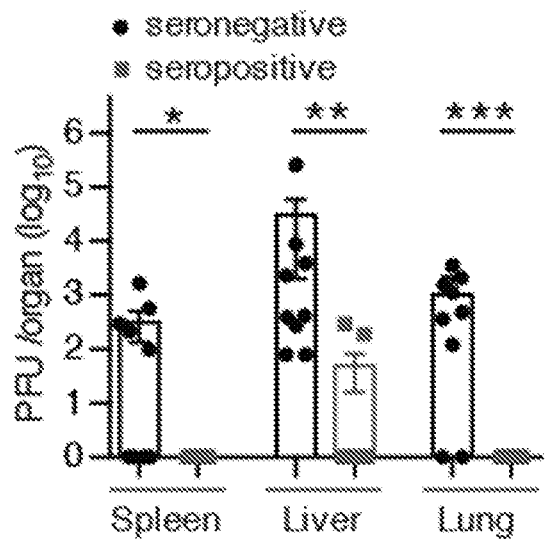
Figure 6:
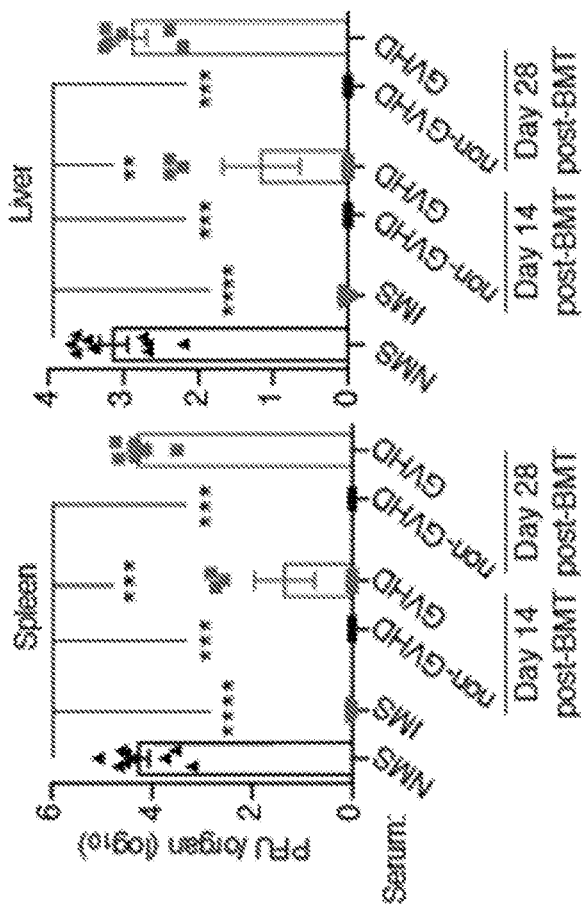
Figure 6:
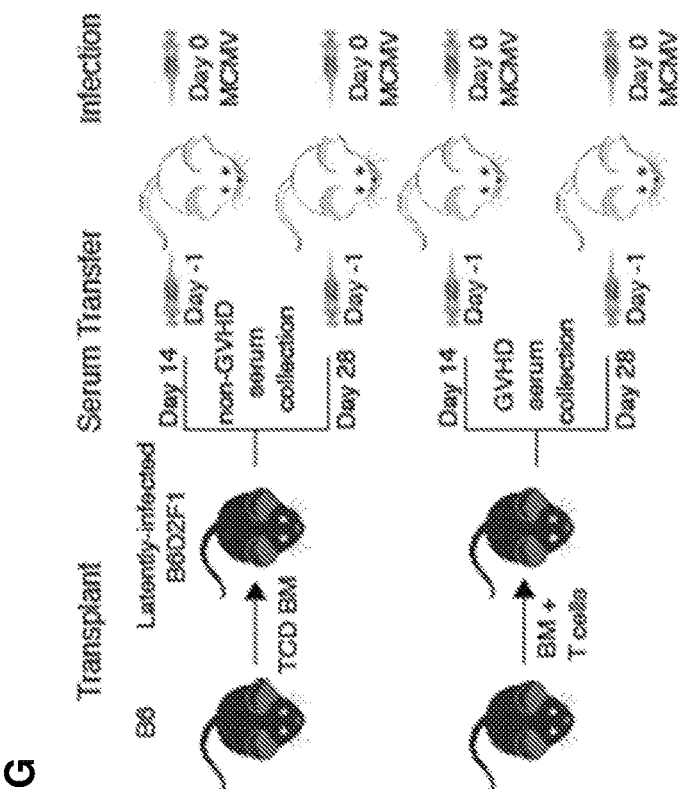
Figure 6:
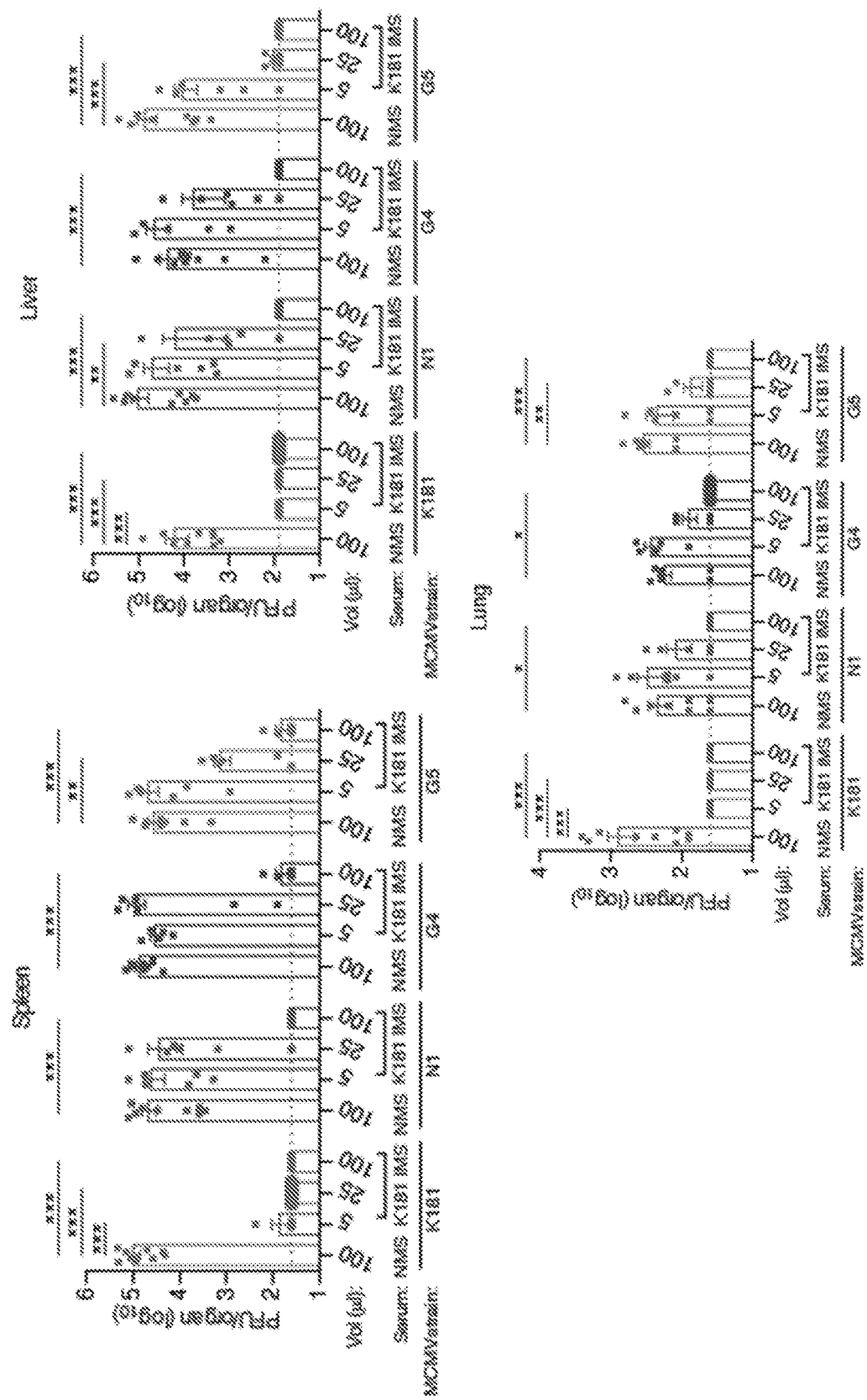
Figure 6:
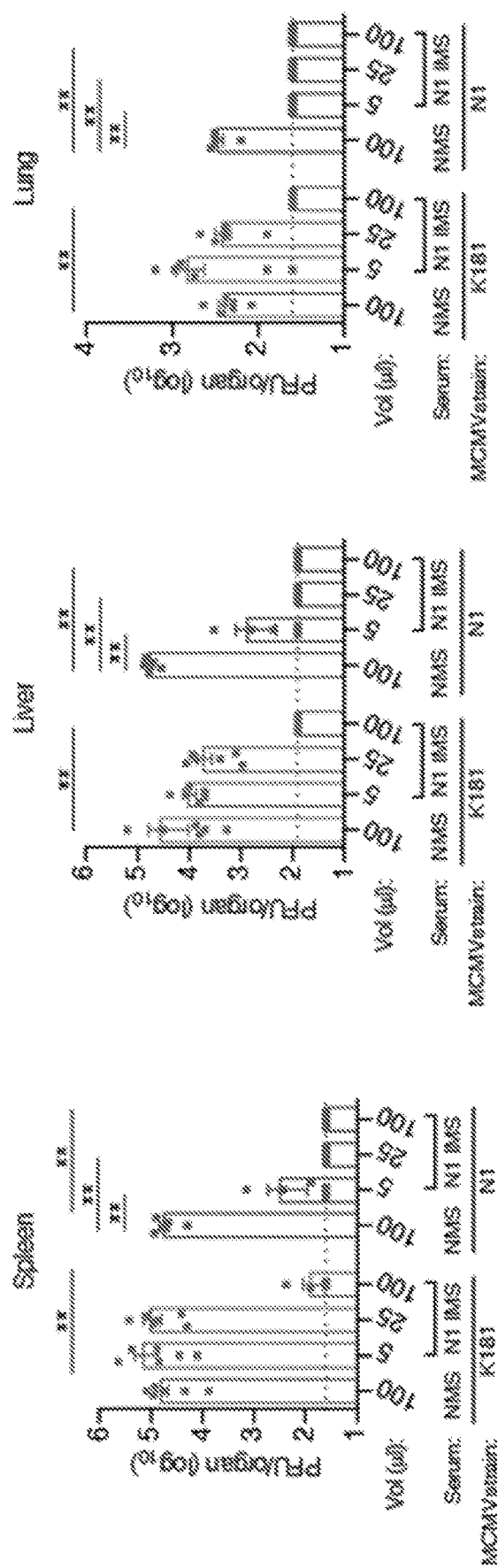
Figure 6:
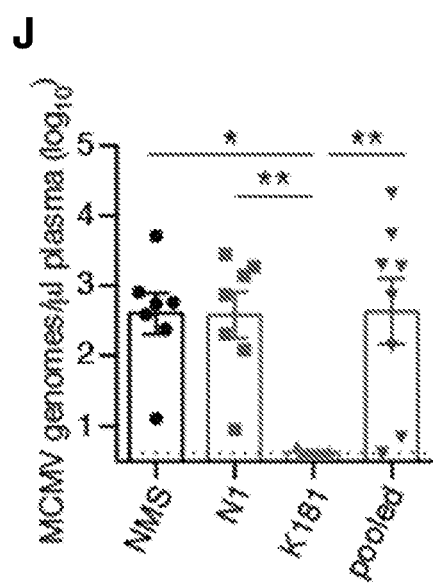
Figure 6:
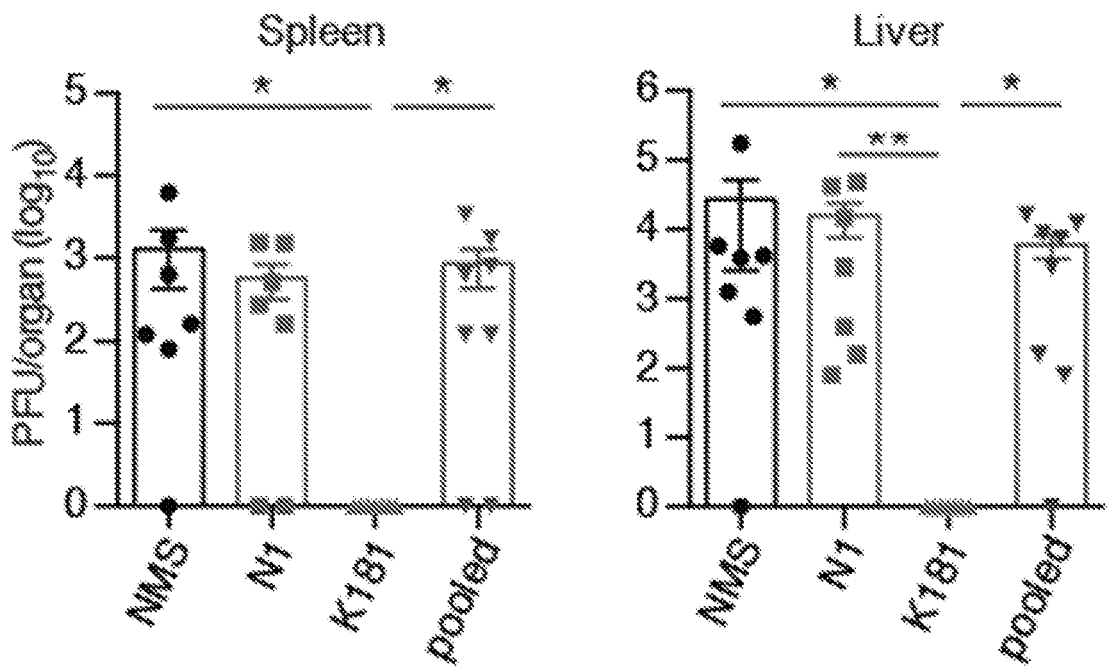
Figure 6:
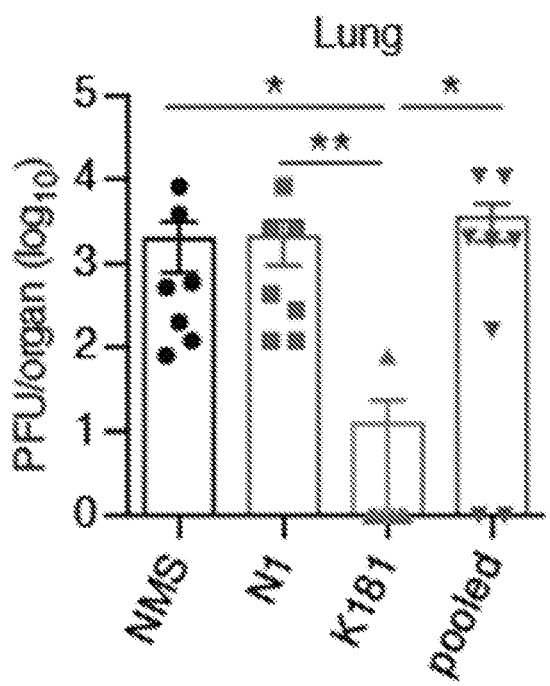

Example 6: Recipient Plasma Cells Persist Post-Transplant and Produce IgG$^{MCMV}$ Antibodies GHVD, and its associated immunosuppressive therapy, results in long-term immune deficiency and impaired infection-specific immunity. In a B6→B6D2F1 BMT system, mature splenic B cells were significantly reduced in recipients with GVHD (FIG. 6A). Plasma cells are known to be long-lived and reported to be resistant to irradiation (Cassese et al., (2003), *Journal of Immunology*, 171: 1684-1690), however our results show that recipient plasma cell numbers and frequencies are greatly reduced in the BM with the onset of GVHD (FIGS. 6B and C). Thus, functional recipient plasma cells persist post-transplant but, they are eliminated with the onset of GVHD (FIG. 6C).

Example 7: Serum Antibodies Protect from MCMV Reactivation Post-Transplant

Latently infected B6D2F1 (H-2$^{b/d}$) mice were transplanted with BM and T cells from haploidentical B6 (H-2$^b$) donors and administered serum from either a latent seropositive or a naïve (seronegative) donor. GHVD clinical scores were similar post-transplant between groups (FIG. 6D) indicating that the adoptive transfer of immune serum did not affect the development of GVHD. At week 3, no MCMV reactivation had occurred in the group of mice which received seropositive serum, and the protective effect was clear by week 4. All mice which received seronegative serum reactivated with detectable plasma viremia and viral titre and essentially no virus was detected in mice which received seropositive donor sera (FIGS. 6E and F). These data show that immune serum completely protects from replicating virus in plasma and organs of transplanted GVHD mice. The present inventors have shown that under GVHD conditions MCMV antibody production is compromised, but it remains unclear whether the antibody response generated under these conditions is able to protect from MCMV reactivation. To address this, the present inventors collected serum from transplanted mice at days 14 and 28 and performed serum transfer experiments in highly susceptible 3 week old BALB/c mice, prior to primary MCMV infection. Serum from mice without GVHD limited viral replication to the same extent as treatment with immune serum (FIG. 6G), whereas serum collected from mice with GVHD showed incomplete protection which diminished over the course of GVHD, such that serum collected at day 28 post-transplant showed no protection, with viral loads in target organs equivalent to those observed in mice that received non-immune serum (FIG. 6G). Altogether, these data demonstrate that the loss of pre-existing antibodies and elimination of recipient plasma cells leads to CMV reactivation in recipients with GVHD.

Previous attempts to ameliorate CMV disease in transplant recipients with immunoglobulins, purified from either normal donors (IVIG) or donors with high titres of CMV antibodies (CMV-IG) have provided ambiguous results. These data suggest the potential requirement for virus-strain specific neutralization/inhibition. This was tested by examining whether immune serum from mice infected with MCMV-K181 afforded protection to infection with unrelated strains. As little as 5 µl of K181 immune serum provided complete protection against infection with the same viral isolate (FIG. 6H). In comparison, protection against infection with three unrelated MCMV isolates (N1, G4 and G5) required immune serum to be administered in significantly higher (5-20-fold) quantities (FIG. 6H). Similar findings were obtained when immune serum from mice latently infected with the N1 isolate was tested in a reverse experimental setting (FIG. 6I). Finally, the capacity of antibodies to protect against reactivation of an antigenically mismatched MCMV strain was tested. Treatment of transplant recipients with K181 serum prevented reactivation of K181 (FIGS. 6J and K). In contrast, serum specific for the N1 isolate, or pooled sera generated by combining serum from mice individually infected with eight different MCMV isolates (including K181), were unable to prevent reactivation of K181 (FIGS. 6J and K). Thus, CMV serotherapy is effective and confers high-level protection, even during GVHD, provided that the antibodies are specific for the infecting CMV isolate. Conversely, dilution of strain-specific antibodies in polyclonal preparations renders them ineffective. This may explain the poor efficacy of polyclonal CMV immunoglobulin therapy observed in clinical studies.

The invention claimed is:

1. A method for inhibiting cytomegalovirus (CMV) reactivation in a transplant recipient with a CMV-seropositive serological status, the method comprising obtaining serum and/or plasma from the transplant recipient prior to transplantation and administering an effective amount of the serum and/or plasma, or a component thereof, to the transplant recipient before, concomitant with or after transplantation, wherein the serum or plasma or component thereof comprises one or more anti-CMV antibodies.

2. The method of claim 1, wherein the transplant is a solid organ transplant.

3. The method of claim 1, wherein the transplant is a bone-marrow transplant or a hematopoietic stem cell transplant.

4. The method of claim 1, wherein the component is an isolated or enriched antibody fraction.

5. The method of claim 1, wherein the component is isolated anti-CMV antibodies.

6. The method of claim 5, wherein the isolated anti-CMV antibodies are IgGCMV antibodies.

7. The method of claim 1, wherein the serum or plasma, or a component thereof, comprises anti-CMV antibodies with specificity to two or more CMV antigens.

8. The method of claim 1, wherein the transplant recipient has graft-versus-host disease (GVHD).

9. The method of claim 1, wherein the anti-CMV antibodies are specific for CMV strains present in the transplant recipient.

10. The method of claim 1, wherein CMV serological status is determined by detecting in the blood sample of the transplant recipient anti-CMV antibodies.

11. The method of claim 1, wherein the transplant donor is CMV-seropositive.

12. The method of claim 11, further comprising obtaining serum and/or plasma from the CMV-seropositive transplant donor and administering an effective amount of the donor serum and/or plasma, or a component thereof, to the transplant recipient before, concomitant with, or after, transplantation, wherein the donor serum or plasma comprises one or more anti-CMV antibodies.

13. The method of claim 12, wherein the anti-CMV antibodies are specific for CMV strains present in the CMV-seropositive transplant donor.

* * * * *